US011857584B2

(12) United States Patent
Ogata et al.

(10) Patent No.: US 11,857,584 B2
(45) Date of Patent: Jan. 2, 2024

(54) ONCOLYTIC VIRUS GROWTH METHOD AND ANTITUMOR AGENT

(71) Applicants: Hisanobu Ogata, Fukuoka (JP); Kenzaburo Tani, Minato-ku (JP); KABUSHIKI KAISHA YAKULT HONSHA, Minato-ku (JP)

(72) Inventors: Hisanobu Ogata, Fukuoka (JP); Kenzaburo Tani, Minato-ku (JP)

(73) Assignees: Hisanobu Ogata, Fukuoka (JP); Kenzaburo Tani, Minato-ku (JP); KABUSHIKI KAISHA YAKULT HONSHA, Minato-ku (JP)

( * ) Notice: Subject to any disclaimer, the term of this patent is extended or adjusted under 35 U.S.C. 154(b) by 1001 days.

(21) Appl. No.: 16/497,705

(22) PCT Filed: Mar. 30, 2018

(86) PCT No.: PCT/JP2018/013974
§ 371 (c)(1),
(2) Date: Sep. 25, 2019

(87) PCT Pub. No.: WO2018/182014
PCT Pub. Date: Oct. 4, 2018

(65) Prior Publication Data
US 2020/0023023 A1    Jan. 23, 2020

(30) Foreign Application Priority Data
Mar. 31, 2017  (JP) ................. 2017-071296

(51) Int. Cl.
*A61K 35/768* (2015.01)
*A61P 35/00* (2006.01)
*A61K 31/282* (2006.01)
*A61K 31/4745* (2006.01)
*A61K 31/513* (2006.01)
*C12N 7/00* (2006.01)

(52) U.S. Cl.
CPC .......... *A61K 35/768* (2013.01); *A61K 31/282* (2013.01); *A61K 31/4745* (2013.01); *A61K 31/513* (2013.01); *A61P 35/00* (2018.01); *C12N 7/00* (2013.01); *C12N 2770/32332* (2013.01)

(58) Field of Classification Search
CPC .................................................. A61K 35/768
See application file for complete search history.

(56) References Cited

U.S. PATENT DOCUMENTS

| 2008/0057036 | A1 | 3/2008 | Johansson et al. |
| 2009/0317456 | A1 | 12/2009 | Karrasch et al. |
| 2010/0297072 | A1 | 11/2010 | DePinho |
| 2012/0134963 | A1 | 5/2012 | Bell et al. |
| 2012/0328575 | A1 | 12/2012 | Johansson et al. |
| 2015/0202240 | A1 | 7/2015 | Bell et al. |
| 2015/0297650 | A1 | 10/2015 | Tani et al. |
| 2016/0120922 | A1 | 5/2016 | Beadle et al. |
| 2016/0136211 | A1 | 5/2016 | Shafren et al. |
| 2016/0143969 | A1* | 5/2016 | Tani ............... A61K 35/768 435/236 |
| 2018/0271921 | A1 | 9/2018 | Hwang et al. |
| 2019/0134120 | A1 | 5/2019 | Shafren et al. |
| 2022/0054563 | A1 | 2/2022 | Beadle et al. |

FOREIGN PATENT DOCUMENTS

| CN | 101027394 A | 8/2007 | |
| CN | 102471300 A | 5/2012 | |
| CN | 105431157 A | 3/2016 | |
| EP | 2851078 * | 4/2013 | ............. A61K 45/06 |
| EP | 2 851 078 A1 | 3/2015 | |
| JP | 2007-527719 A | 10/2007 | |
| JP | 2008-526188 A | 7/2008 | |
| JP | 2012-46489 A | 3/2012 | |
| JP | 2016-526531 A | 9/2016 | |
| WO | WO 2004/054613 A1 | 7/2004 | |
| WO | WO 2005/087931 A1 | 9/2005 | |
| WO | WO2008/043576 * | 2/2008 | ............. A61K 45/06 |
| WO | WO 2008/043576 A1 | 4/2008 | |
| WO | WO2010/135242 * | 11/2010 | ............. A61K 45/06 |
| WO | WO 2010/135242 A1 | 11/2010 | |
| WO | WO 2013/157648 A1 | 10/2013 | |
| WO | WO 2014/171526 A1 | 10/2014 | |
| WO | WO2014/201492 * | 12/2014 | ............. A61K 45/06 |
| WO | WO 2014/201492 A1 | 12/2014 | |
| WO | WO2015/155263 * | 10/2015 | ............. A61K 45/06 |
| WO | WO 2015/155263 A1 | 10/2015 | |
| WO | WO2017/043815 * | 3/2017 | ............. A61K 45/06 |
| WO | WO 2017/043815 A1 | 3/2017 | |

OTHER PUBLICATIONS

Combined Chinese Office Action and Search Report dated Mar. 2, 2022 in Chinese Patent Application No. 201880020318.2 (with English translation), 23 pages.
Rauf Bhat, et al., "Emerging Role of Natural Killer Cells in Oncolytic Virotherapy" ImmunoTargets and Therapy, No. 4, Mar. 31, 2015, pp. 65-77.
International Search Report dated May 29, 2018 in PCT/JP2018/013974 filed Mar. 30, 2018.
Tani, K., "Chemotherapy and gene therapy," Clinic All-Round, vol. 50, No. 2, 2001, pp. 210-215 (with partial English translation).
Ottolino-Perry, K. et al., "Oncolytic vaccinia virus synergizes with irinotecan in colorectal cancer," Molecular Oncology, vol. 9, 2015, pp. 1539-1552.
Extended European Search Report dated Nov. 6, 2020 in corresponding European Patent Application No. 18778015.0, 10 pages.
Office Action dated Jan. 25, 2022 in corresponding Japanese Patent Application No. 2019-509428 (with English Translation), 23 pages.

(Continued)

*Primary Examiner* — Paul V Ward
(74) *Attorney, Agent, or Firm* — Oblon, McClelland, Maier & Neustadt, L.L.P.

(57) ABSTRACT

Provided is antitumor therapy using oncolytic viruses which exhibits an excellent antitumor effect and has reduced adverse effects.
An antitumor agent, comprising a combination of an oncolytic virus and an anticancer agent selected from the group consisting of oxaliplatin, an anticancer plant alkaloid, and an antimetabolite.

8 Claims, 9 Drawing Sheets

Specification includes a Sequence Listing.

(56) References Cited

OTHER PUBLICATIONS

Joe Goldufsky et al., "Oncolytic virus therapy for cancer", Oncolylic Virotherapy, vol. 2, 2013, pp. 31-46.

* cited by examiner

1. Oxaliplatin 0 μM (no addition)
2. Oxaliplatin 0.25 μM
2. Oxaliplatin 0.5 μM
4. Oxaliplatin 1.0 μM
5. Oxaliplatin 2.5 μM

ONCOLYTIC VIRUS GROWTH METHOD AND ANTITUMOR AGENT

FIELD OF THE INVENTION

The present invention relates to a novel antitumor therapy using oncolytic viruses.

BACKGROUND OF THE INVENTION

Malignant tumor is the primary cause of death for Japanese, and statistically one in three people dies of malignant tumor. Efforts over the years have led to significant advances in surgical therapy, radiation therapy, and chemotherapy including molecular targeted therapy against malignant tumors and have improved outcomes. However, the mortality rate of malignant tumors remains still high, and there is a need for a new therapeutic method effective for malignant tumors.

As a new therapeutic method, oncolytic virus therapy has attracted attention because of its direct cytocidal effect. For example, clinical trials using oncolytic adenoviruses and herpes simplex viruses that are DNA viruses have been conducted for the treatment of brain tumor and breast cancer, and results suggesting safety and efficacy have been reported.

In addition, enteroviruses of the Picornaviridae that are RNA viruses do not integrate into the genome of host cells after infection, have little risk of malignant transformation due to gene mutation, have no oncogene, and thus are highly safe. Further, the enteroviruses have a high proliferation rate in cells, and thus are expected to show a rapid and high antitumor effect. For example, oncolytic virus therapy using enteroviruses such as coxsackievirus (CV) A21, echovirus (EV) 6, EV7, EV11, EV12, EV13, and EV29 (Patent Literature 1), oncolytic virus therapy using CVA13, CVA1S, CVA18, CVA21, EV1, EV7, EV8, and EV22 (Patent Literature 2) and the like have been reported.

Furthermore, the present inventors have recently found that coxsackievirus A11 (referred to as "CVA11") and echovirus 4 (referred to as "EV4") are viruses exhibiting high cytotoxicity to tumour cells as well as low pathogenicity and high safety to humans (Patent Literature 3).

CITATION LIST

Patent Literature

Patent Literature 1: JP-A-2007-527719
Patent Literature 2: JP-A-2012-46489
Patent Document 3: WO2013/157648

SUMMARY OF THE INVENTION

Problems to be Solved by the Invention

The present invention relates to providing antitumor therapy using oncolytic viruses which exhibits an excellent antitumor effect and has reduced adverse effects.

Means for Solving the Problems

The present inventors conducted repeated research on oncolytic virus therapy, and as a result, found that the use of a specific anticancer agent in combination with a coxsackievirus or the like promotes the proliferation of the virus and remarkably enhances the antitumor effect of the virus without increasing adverse effects.

That is, the present invention includes the following 1) to 18).

1) An antitumor agent, comprising a combination of an oncolytic virus and an anticancer agent selected from the group consisting of oxaliplatin, an anticaner plant alkaloid, and an antimetabolite.
2) The antitumor agent according to 1), wherein the oncolytic virus is a coxsackievirus or an adenovirus.
3) The antitumor agent according to 2), wherein the coxsackievirus is coxsackievirus A11 or coxsackievirus B3.
4) The antitumor agent according to any one of 1) to 3), wherein the anticancer plant alkaloid is one or more selected from the group consisting of SN-38, irinotecan, and a salt thereof.
5) The antitumor agent according to any one of 1) to 3), wherein the antimetabolite is 5-FU or a salt thereof.
6) An antitumor agent, comprising an oncolytic virus and an anticancer agent selected from the group consisting of oxaliplatin, an anticancer plant alkaloid, and an antimetabolite.
7) The antitumor agent according to 6), wherein the oncolytic virus is a coxsackievirus or an adenovirus.
8) The antitumor agent according to 7), wherein the coxsackievirus is coxsackievirus A11 or coxsackievirus B3.
9) The antitumor agent according to any one of 6) to 8), wherein the anticancer plant alkaloid is one or more selected from the group consisting of SN-38, irinotecan, and a salt thereof.
10) The antitumor agent according to any one of 6) to 8), wherein the antimetabolite is 5-FU or a salt thereof.
11) The antitumor agent according to any one of 1) to 5), which is a kit comprising a drug comprising the oncolytic virus and a drug comprising the anticancer agent selected from the group consisting of oxaliplatin and an anticancer plant alkaloid.
12) An agent for enhancing an antitumor effect of an oncolytic virus, comprising, as an active ingredient, an anticancer agent selected from the group consisting of oxaliplatin, an anticancer plant alkaloid, and an antimetabolite.
13) The agent for enhancing an antitumor effect according to 12), wherein the oncolytic virus is a coxsackievirus or an adenovirus.
14) A method for promoting the proliferation of an oncolytic virus, comprising culturing an oncolytic virus in the presence of an anticancer agent selected from the group consisting of oxaliplatin, an anticancer plant alkaloid, and an antimetabolite.
15) An agent for enhancing the expression of a virus receptor of a cancer cell, comprising, as an active ingredient, an anticancer agent selected from the group consisting of oxaliplatin, an anticancer plant alkaloid, and an antimetabolite.
16) The agent for enhancing the expression of a virus receptor according to 15), wherein the virus receptor is DAF and/or ICAM-1.
17) Use of an oncolytic virus and an anticancer agent selected from the group consisting of oxaliplatin, an anticancer plant alkaloid, and an antimetabolite, for the production of an antitumor agent.
18) A combination of an oncolytic virus and an anticancer agent selected from the group consisting of oxaliplatin, an anticancer plant alkaloid, and an antimetabolite, for use in antitumor therapy.

19) Antitumor therapy, comprising administering an oncolytic virus and an anticancer agent selected from the group consisting of oxaliplatin, an anticancer plant alkaloid, and an antimetabolite to a patient.

Effects of the Invention

According to the present invention, it is possible to provide antitumor therapy which exhibits an excellent antitumor effect and is highly safe for humans.

MODES FOR CARRYING OUT THE INVENTION

Figure 1:
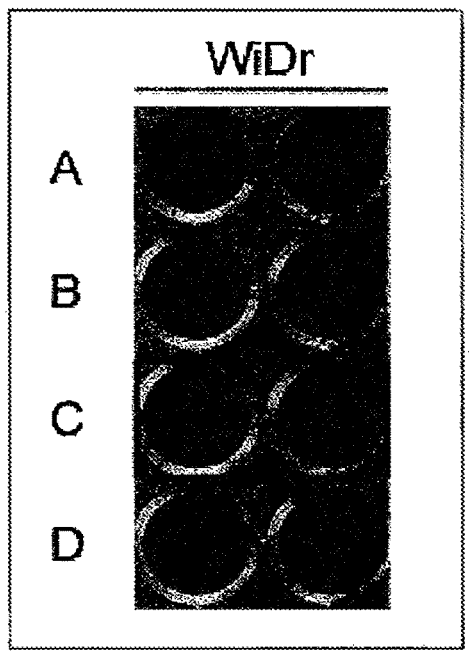
FIG. 1 shows cytotoxicity against oxaliplatin-resistant colon cancer cell line (WiDr). A: neither oxaliplatin nor CVA11 was added, B: oxaliplatin only was added (50 µM), C: oxaliplatin was added (50 µM), and then CVA11 was added (MOI (multiplicity of infection)=0.01), and D: CVA11 only was added (MOI=0.01).

Oncolytic viruses are viruses that infect cancer cells to thereby cause the lysis and death of the cancer cells. The oncolytic viruses of the present invention are not particularly limited as long as they are viruses that can cause the lysis and death of cancer cells. Examples thereof include enteroviruses such as CVA11, CVB3 (coxsackievirus) and EV4 (echovirus), adenoviruses such as AAV, and herpes simplex virus variants such as HF10, and CVA11, CVB3, and AAV are particularly preferable. CVA11 and CVB3 are coxsackieviruses, a type of enteroviruses belonging to the Picornaviridae family. Coxsackieviruses are classified into two groups, group A and group B, group A is further classified into 24 types, and group B is further classified into 6 types. CVA11 of the present invention is a coxsackievirus of group A and type 11 and CVB3 is a coxsackievirus of group B and type 3.

The oncolytic viruses can infect cells by binding to virus receptors on the cell surface. Examples of the virus receptors include decay accelerating factor (DAF or CD55), intercellular adhesion molecule-1 (ICAM 1 or CD54), and integrin $\alpha_2\beta_1$ (CD49b). The interaction of the oncolytic viruses with the virus receptors destabilizes the capsid, thereby inducing the uncoating of the oncolytic viruses.

The oncolytic viruses can be isolated from a sample or the like by a known virus isolation method such as centrifugal separation or virus proliferation using cultured cells. The oncolytic viruses of the present invention may also be biologically selected by culturing naturally occurring viruses in a cell line over multiple passages so as to obtain high infectivity to cancer cells. As the cell line suitable for biological selection, those having virus receptors such as DAF, ICAM-1, and integrin $\alpha_2\beta_1$ are preferred, and examples thereof include HEK293 cells, H1299 cells, A549 cells, LK-87 cells, PC-9 cells, and H460 cells.

The oncolytic viruses of the present invention may be naturally occurring viruses, modified viruses, or partially mutated viruses. In addition to the normal viruses, vector-type viruses may also be used. Examples of a variant of CVA11 include those in which the capsid is removed. The capsid can be removed, for example, by treatment with a protease such as chymotrypsin or trypsin. Specifically, for example, the capsid can be removed by treating CVA11 with chymotrypsin in the presence of a surfactant such as an alkyl sulfate. Removal of the capsid from CVA11 can increase the infectivity of the virus to cancer cells. Also, since the proteins present in the capsid are the main activators for the humoral and cellular immunity of a host, the removal of the capsid from CVA11 can reduce the immune response of the host. As a result, it is possible to improve the infectivity of CVA11 to cancer cells and the cytotoxicity of the pharmaceutical composition to the cancer cells.

In the present invention, the oncolytic viruses include a nucleic acid derived from the oncolytic viruses that infect cancer cells. The nucleic acid derived from the oncolytic viruses includes virus RNA directly isolated from the oncolytic viruses, synthetic RNA, and cDNA corresponding to the nucleotide sequence of the isolated virus RNA.

For the isolation of virus RNA, any method such as phenol/chloroform extraction or isolation by magnetic beads can be used.

Further, the nucleic acid may also be a virus plasmid or an expression vector into which a nucleic acid for generating a virus is incorporated. The expression vector includes, for example, a plasmid capable of expressing DNA encoding a virus protein required for virus production. The expression vector may include a transcriptional regulatory control sequence to which the inserted nucleic acid is operably linked. The transcriptional regulatory control sequence in this case includes, for example, a promoter for initiating transcription, an expression control element for allowing the binding of ribosomes to the transcribed mRNA, and the like.

The nucleic acid derived from CVA11 of the coxsackieviruses specifically includes a nucleic acid comprising the nucleotide sequence of SEQ ID NO: 1. The nucleic acid derived from CVB3 specifically includes a nucleic acid comprising the nucleotide sequence of SEQ ID NO: 2. As the expression vector, for example, pSV2neo, pEF-PGk.puro, pTk2, a non-replicating adenovirus shuttle vector, a cytomegalovirus promoter, or the like can be used. The cDNA encoding a virus protein required for virus production can be prepared by reverse transcription of virus RNA or a fragment thereof.

The nucleic acid derived from AAV of the adenoviruses specifically includes a nucleic acid comprising the nucleotide sequence of SEQ ID NO: 3. As the expression vector, for example, pSV2neo, pEF-PGk.puro, pTk2, a non-replicating adenovirus shuttle vector, a cytomegalovirus promoter, or the like can be used. The cDNA encoding a virus protein required for virus production can be prepared by reverse transcription of virus RNA or a fragment thereof.

In the present invention, the anticancer agent is selected from the group consisting of oxaliplatin, an anticancer plant alkaloid, and an antimetabolite. Examples of the anticancer plant alkaloid include vincristine, vinblastine, vindesine, vinorelbine, etoposide, irinotecan or an active metabolite thereof or a salt thereof, nogitecan, sobuzoxane, docetaxel, paclitaxel, paclitaxel injection, and elibrin, and irinotecan, SN-38, or a salt thereof is preferable. In addition, examples of the antimetabolite include fluoropyrimidine anticancer agents such as 5-fluorouracil (5-FU), a prodrug of 5-FU (e.g., tegafur or a salt thereof), capecitabine or a salt thereof, TS-1 (also referred to as S-1, a compounding preparation including tegaful and a modulator), carmoful, and doxifluridine; gemcitabine, cytarabine, enocitabine, mercaptopurine, fludarabine, cladribine, methotrexate, pemetrexed, hydroxycarbamide, nelarabine, pentostatin, and a prodrug thereof, and fluoropyrimidine anticancer agents which allow 5-fluorouracil to be present in vivo are more preferable, and 5-FU or a salt thereof is particularly preferable.

Oxaliplatin is a third-generation platinum-complex anticancer agent, also known as L-OHP. In the present invention, "oxaliplatin" includes cis-oxaloto(trans-1-1,2-diaminocyclohexane)platinum(II), cis-oxaloto(trans-d-1,2-diaminocyclohexane)platinum(II), which is an optical enantiomer thereof, and a mixture thereof.

Irinotecan is a derivative of camptothecin, which is an antitumor alkaloid derived from *Camptotheca acuminata*, and has a topoisomerase I inhibitory effect. SN-38 (7-ethyl-10-hydroxycamptothecin) is an active metabolite of irinotecan and has a more potent antitumor activity than irinotecan.

As the salt of irinotecan and SN-38, a salt with an inorganic acid or organic acid may be mentioned, but is preferably a hydrochloride.

5-FU is a fluoropyrimidine-based antimetabolite that exerts an antitumor effect by inhibiting nucleic acid synthesis.

Among the above-mentioned anticancer agents, oxaliplatin is preferable. Oxaliplatin, SN-38, and 5-FU have antitumor effects on their own, but as shown in Examples described later, oxaliplatin has an effect of promoting the proliferation of oncolytic viruses, in particular coxsackieviruses, and an effect of enhancing the expression of virus receptors (DAF, ICAM-1) in cancer cells. Further, oxaliplatin, an anticancer plant alkaloid such as SN-38, and an antimetabolite such as 5-FU, when used in combination with a coxsackievirus and oxaliplatin, exhibit much more potent cytotoxicity to oxaliplatin-resistant cancer cells than the case where the coxsackievirus only is used. This is considered to result from the enhancement of the antitumor effect of the coxsackievirus by oxaliplatin, SN-38, or 5-FU.

That is, in the case of combination use of oxaliplatin, an anticancer plant alkaloid, or an antimetabolite and an oncolytic virus, an anticancer agent selected from the group consisting of oxaliplatin, an anticancer plant alkaloid, and an antimetabolite can be an agent for promoting the proliferation of the oncolytic virus, and the combination of the oncolytic virus and the anticancer agent selected from the group consisting of oxaliplatin, an anticancer plant alkaloid, and an antimetabolite can be an antitumor agent (hereinafter, these may also be collectively referred to as "antitumor therapy" of the present invention). In addition, the anticancer agent selected from the group consisting of oxaliplatin, an anticancer plant alkaloid, and an antimetabolite can be an agent for enhancing the expression of a virus receptor of a cancer cell.

Herein, the effect for promoting the proliferation of an oncolytic virus by an anticancer agent selected from the group consisting of oxaliplatin, an anticancer plant alkaloid, and an antimetabolite is obtained by culturing the oncolytic virus together with the anticancer agent selected from oxaliplatin, an anticancer plant alkaloid, and an antimetabolite. For culturing, a known method such as virus proliferation using cultured cells can be used. The effect for promoting the proliferation can be evaluated by using a known method for calculating multiplicity of infection (MI) of virus.

The antitumor effect (cytotoxicity to cancer cells) of the oncolytic virus and the anticancer agent selected from the group consisting of oxaliplatin, an anticancer plant alkaloid, and an antimetabolite of the present invention can be confirmed by testing the survival of a cell line of cancer cells exposed to the oncolytic virus in the presence of the anticancer agent. Examples of a method for testing the survival of the cell line include a method involving staining fixed cells with a stain solution and quantifying the number of stained viable cells, a crystal violet method, and a method involving quantifying an apoptosis specific marker. If the cell line of cancer cells is incubated with the oncolytic virus in the presence of the anticancer agent and the cancer cells that survive after a predetermined period of time is quantified by these methods, cancer cells that died due to cytotoxicity of the oncolytic virus and the anticancer agent can be quantified.

The type of cancer which the antitumor therapy of the present invention targets is not particularly limited as long as the oncolytic virus infects cancer cells and exerts cytotoxicity, and includes solid cancers and humoral cancers.

Examples of cancer cells of solid cancers in which particularly potent cytotoxicity is induced include cancer cells of cancer such as small cell lung cancer, non-small cell lung cancer, squamous cell lung cancer, malignant mesothelioma, colon cancer, colorectal cancer, gastric cancer, esophageal cancer, hypopharyngeal cancer, breast cancer, cervical cancer, ovarian cancer, prostate cancer, or bladder cancer. In addition to the above-mentioned solid cancers, cancer cells of cancer such as non-Hodgkin's lymphoma, lymphocytic leukemia, or human B lymphoma are preferably used as the target of the antitumor therapy of the present invention, and cancer cells of colon cancer or colorectal cancer are particularly preferably used.

In addition, the antitumor therapy of the present invention can also be used for the treatment of cancers resistant to oxaliplatin, an anticancer plant alkaloid, or an antimetabolite, that is, refractory cancers. For example, oxaliplatin-resistant cancers are cancers in which, for example, administration of oxaliplatin at a clinically effective dose does not result in the reduction or suppression of increase in tumor volume or in the improvement of conditions associated with the cancers, and such a cancer is found in small cell lung cancer, non-small cell lung cancer, squamous cell lung cancer, malignant mesothelioma, colon cancer, colorectal cancer, gastric cancer, esophageal cancer, hypopharyngeal cancer, breast cancer, cervical cancer, ovarian cancer, prostate cancer, bladder cancer, non-Hodgkin's lymphoma, lymphocytic leukemia, human B lymphoma, and the like.

In the antitumor therapy of the present invention, the oncolytic virus and the anticancer agent selected from the group consisting of oxaliplatin, an anticancer plant alkaloid, and an antimetabolite may be formulated into a single dosage form, i.e., a compounding agent, comprising an effective amount of each component in an appropriate ratio (one dosage form), or may be formulated as a combination of separate preparations, one comprising an effective amount of the oncolytic virus and the other comprising an effective amount of the anticancer agent so that they can be used simultaneously or separately at intervals (two dosage form; referred to as a kit). The compounding agent may comprise a carrier, a diluent, an adjuvant, or a support, in addition to the oncolytic virus and the anticancer agent selected from the group consisting of oxaliplatin, an anticancer plant alkaloid, and an antimetabolite. As the carrier, for example, a liposome, a micelle, or the like is preferable. The liposome comprises a combination of a lipid and a steroid or steroid precursor that contributes to membrane stability. In this case, examples of the lipid include phosphatidyl compounds such as phosphatidylglycerol, phosphatidylcholine, phosphatidylserine, sphingolipid, phosphatidylethanolamine, cerebroside, and ganglioside. The oncolytic virus coated with liposomes or micelles can reduce the immune response of the host. Examples of the diluent include demineralized water, distilled water, and physiological saline, and examples of the adjuvant include a vegetable oil, a cellulose derivative, polyethylene glycol, and a fatty acid ester. Examples of the support include those conventionally used in ordinary preparations such as an excipient, a binder, a disintegrant, a lubricant, a diluent, a dissolution aid, a suspending agent, an isotonic agent, a pH adjusting agent, a buffer, a stabilizer, a colorant, a corrigent, and a flavoring agent. Further, the compounding agent can be administered in combination with another agent other than the compounding agent.

Also, the kit can be administered in combination with another agent other than the preparation comprising the oncolytic virus and the preparation comprising the anticancer agent selected from the group consisting of oxaliplatin, an anticancer plant alkaloid, and an antimetabolite.

The above-described preparation comprising the oncolytic virus may comprise, in addition to the oncolytic virus, a carrier, a diluent, an adjuvant, or the like. As the carrier, for example, a liposome, a micelle, or the like is preferable. The liposome comprises a combination of a lipid and a steroid or steroid precursor that contributes to membrane stability. In this case, examples of the lipid include phosphatidyl compounds such as phosphatidylglycerol, phosphatidylcholine, phosphatidylserine, sphingolipid, phosphatidylethanolamine, cerebroside, and ganglioside. The oncolytic virus coated with liposomes or micelles can reduce the immune response of the host.

Examples of the diluent include demineralized water, distilled water, and physiological saline, and examples of the adjuvant include a vegetable oil, a cellulose derivative, polyethylene glycol, and a fatty acid ester.

Further, the preparation comprising an anticancer agent selected from the group consisting of oxaliplatin, an anticancer plant alkaloid, and an antimetabolite can be prepared by a conventionally known method using a pharmacologically acceptable carrier. Examples of the carrier include those conventionally used in ordinary preparations such as an excipient, a binder, a disintegrant, a lubricant, a diluent, a dissolution aid, a suspending agent, an isotonic agent, a pH adjusting agent, a buffer, a stabilizer, a colorant, a corrigent, and a flavoring agent.

The incorporation amount of the oncolytic virus in the above-described preparation is, for example, $1 \times 10^2$ to $1 \times 10^{10}$ plaque forming units per 1 ml of a solution, and is preferably $1 \times 10^5$ plaque forming units or more. The incorporation amount of the anticancer agent selected from the group consisting of oxaliplatin, an anticancer plant alkaloid, and an antimetabolite is preferably, for example, 1 to 1000 mg in the preparation.

In the antitumor therapy of the present invention, the oncolytic virus and the anticancer agent selected from the group consisting of oxaliplatin, an anticancer plant alkaloid, and an antimetabolite can be administered to a cancer patient by various methods, i.e., oral, intramuscular, subcutaneous, rectal, vaginal, nasal cavity administration, or the like, but it is preferable to administer them intratumorally, intravenously, or intraperitoneally depending on the type of cancer. In particular, in the case of many gastrointestinal cancers such as esophageal cancer and colon cancer, the above-described preparation composition can be injected directly into the tumor tissue while viewing the tumor tissue with an endoscope or the like. In this case, since the injection site can be confirmed with an endoscope or the like, there is an advantage that it is easy to control bleeding.

The oncolytic virus and the anticancer agent selected from the group consisting of oxaliplatin, an anticancer plant alkaloid, and an antimetabolite may be administered in an amount sufficient to treat cancer, and the dose is determined based on the weight, age, sex, size of tumor tissue, and the like of the patient. For example, the daily dose of the oncolytic virus for an adult can be $1 \times 10^2$ to $1 \times 10^{10}$ plaque forming units and the daily dose of the anticancer agent for an adult can be 1 to 1000 mg.

The administration method may be a single administration or multiple administrations, and may also be a continuous administration of a sustained release preparation. In addition, the order of administration and the interval of administration are not particularly limited as long as the effect of the combination of the oncolytic virus and the anticancer agent selected from the group consisting of oxaliplatin, an anticancer plant alkaloid, and an antimetabolite can be obtained, but it is more preferable to administer the oncolytic virus after administration of the anticancer agent selected from the group consisting of oxaliplatin, an anticancer plant alkaloid, and an antimetabolite. In the case of a kit, each single preparation may be administered simultaneously or at intervals.

EXAMPLES

The present invention will be explained specifically by way of Examples below, but the present invention is not limited thereto.

Example 1 Antitumor Effect of Combination of Oxaliplatin and CVA11

(1) Method
(a) Preparation of CVA11
CVA11 was obtained from the National Institute of Infectious Diseases. CVA11 was proliferated using HELA cells (purchased from ATCC). CVA11 (seeding amount: MOI=0.1 to 1.0) was incubated for 1 hour on HELA cells (about 2×10$^6$ cells/mL) subcultured with 10 ml of Dulbeccors modified Eagle medium (DMEM) (manufactured by Sigma-Aldrich), then the medium was replaced with DMEM, and the resultant was allowed to stand until a cytopathic effect was observed. After removing the medium, 1 mL of OPTI-MEM I was added to the culture dish, and the cells were detached and collected using a cell scraper. It should be noted that CVA11 and HELA cells were cultured in an incubator at 37° C., 5% $CO_2$. After freezing and thawing of the collected HELA cells were repeated three times using liquid nitrogen, the supernatant was collected by centrifugation at 3000 rpm for 15 minutes at 4° C. The collected supernatant (virus solution) was stored at −80° C.

(b) Calculation of MOI

The MOI was calculated by the following method as described in Patent Literature 3.

An oxaliplatin-resistant colon cancer cell line (WiDr) (obtained from ATCC) was seeded in a 96-well plate at 5×10$^3$ cells/100 μL/well and maintained for 5 hours at 37° C., 5% $CO_2$. Viruses were diluted 100- or 1000-fold with OPTI-MEM I to prepare a virus stock solution for MOI measurement (the common logarithm of the dilution factor here was taken as "L"). The virus stock solution was serially diluted 10-fold (the common logarithm of the dilution factor here was taken as "d") to prepare serially diluted solutions. Next, 0.05 mL of the serially diluted solution was added to each well (the volume of the serially diluted solution added was taken as "v"). A value "S" was obtained by dividing the total number of wells in which a cytopathic effect of 50% or more was observed after 120 hours by 8, and the MOI was calculated by the following formula.

Log 10(MOI)=L+d(S−0.5)+log 10(1/v)    (Formula 1)

(c) Study on Antitumor Effect of CVA11 Using Crystal Violet Method

The antitumor effect (cytotoxicity) of CVA11 was evaluated by the crystal violet method.

The oxaliplatin-resistant colon cancer cell line (WiDr) was seeded in a 24-well plate at a density (3×10$^4$ cells/well) becoming confluent after 72 hours. For the preparation of a diluted solution of CVA11, CVA11 was diluted with OPTI-MEM I so as to accomplish an appropriate multiplicity of infection (MOI=0.001, 0.01, or 0.1). After about 6 hours, the medium was removed from the plate, 200 μl of the diluted solution of CVA11 was added to each well, and the plate was maintained for 1 hour at 37° C., 5% $CO_2$. Next, the diluted solution of CVA11 was removed, and 1 ml of cell culture medium was added to each well, followed by culturing for 72 hours. After 72 hours, the cells were washed gently with phosphate buffered saline (PBS), 300 μL of PBS containing 0.5% glutaraldehyde was added to each well, and then the plate was allowed to stand for 15 minutes at room temperature to fix viable adherent cells. Thereafter, the PBS containing glutaraldehyde was removed, washing with PBS was performed, and then 300 μL of sterile water containing 2% ethanol and 0.1% crystal violet was added to each well, followed by standing for 10 minutes at room temperature, to thereby stain the viable cells. Each well of the plate after staining was washed twice with 500 μL of sterile water, and staining was recorded using a scanner to confirm the antitumor effect.

The following four groups were prepared and compared: A: neither oxaliplatin nor CVA11 was not added, B: oxaliplatin only was added (50 μM), C: oxaliplatin was added (50 μM) and then CVA11 was added (MOI=0.01), and D: CVA11 only was added (MOI=0.01).

(2) Result

FIG. 1 shows the results by the crystal violet method. No antitumor effect was observed in group B to which oxaliplatin only was added, and in group D to which CVA11 only was added. In contrast, a potent antitumor effect was observed in group C to which oxaliplatin was added and then CVA11 was added (MOI=0.01).

Example 2 Effect of Oxaliplatin for Promoting Proliferation of CVA11

(1) Method

The cultured oxaliplatin-resistant colon cancer cell line (WiDr) was suspended in DMEM medium at 3×10$^6$ cells/mL. To each well of a 96-well plate, 100 μl of the obtained cell suspension was dispensed and the cells were seeded at 3×10$^5$ cells/well. The plate was allowed to stand for about 8 hours at 37° C., 5% $CO_2$, and then oxaliplatin was added thereto at a final concentration of 50 μM. Subsequently, the plate was allowed to stand for about 12 hours at 37° C., 5% $CO_2$, and then CVA11 was added thereto at a MOI of 0.01. After the plate was allowed to stand for about 30 hours at 37° C., 5% $CO_2$, multiplicity of infection of the virus was measured by the method as described in Example 1(1)(b). The following three groups were prepared and compared: A: neither oxaliplatin nor CVA11 was not added, B: oxaliplatin was not added and CVA11 only was added, and C: oxaliplatin was added (50 μM) and then CVA11 was added (MOI=0.01). The t-test was used as the test.

(2) Result

Figure 2:
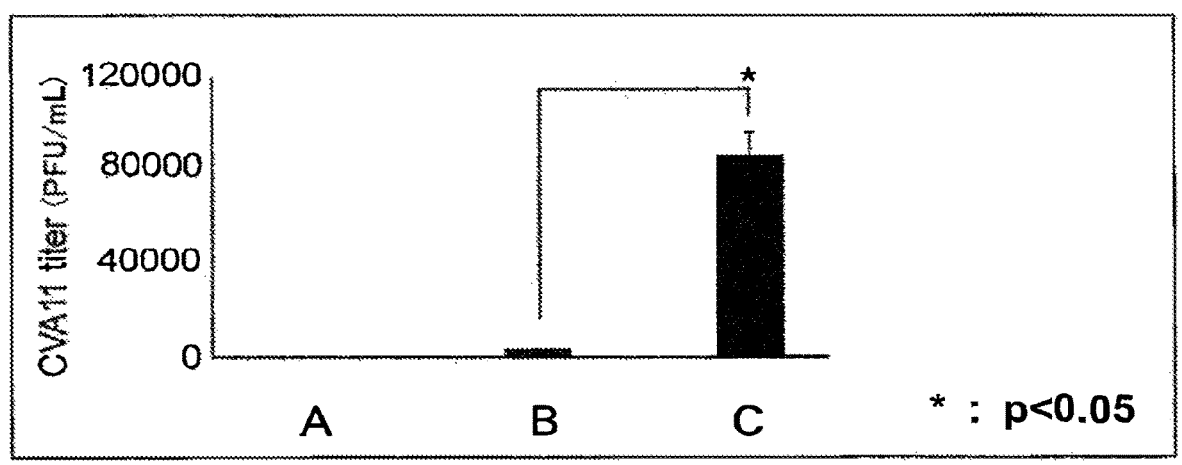
FIG. 2 shows that oxaliplatin promotes the proliferation of CVA11.

FIG. 2 shows the results of virus titers of CVA11. In the group to which oxaliplatin was added, a significant increase in CVA11 virus load was observed. It was confirmed that oxaliplatin promotes the proliferation of CVA11.

Example 3 Effect of Oxaliplatin for Enhancing Expression of Virus Receptor (1) Method The cultured oxaliplatin-resistant colon cancer cell line (WiDr) was suspended in DMEM medium at 3×10$^6$ cells/mL. To each well of a 96-well plate, 100 μl of the obtained cell suspension was dispensed and the cells were seeded at 3×10$^5$ cells/well. After the plate was allowed to stand for about 8 hours at 37° C., 5% $CO_2$, oxaliplatin was added thereto at a final concentration of 50 μM. Thereafter, the plate was allowed to stand for about 42 hours at 37° C., 5% $CO_2$, and then mRNA was collected to prepare cDNA. The cDNA was compared with that of the case where CVA11 was added about 20 hours after seeding the cells. The expressions of DAF (decay accelerating factor) and ICAM-1 (intercellular adhesion molecule 1) were compared by real-time PCR. The t-test was used as the test.

(2) Result

Figure 3:
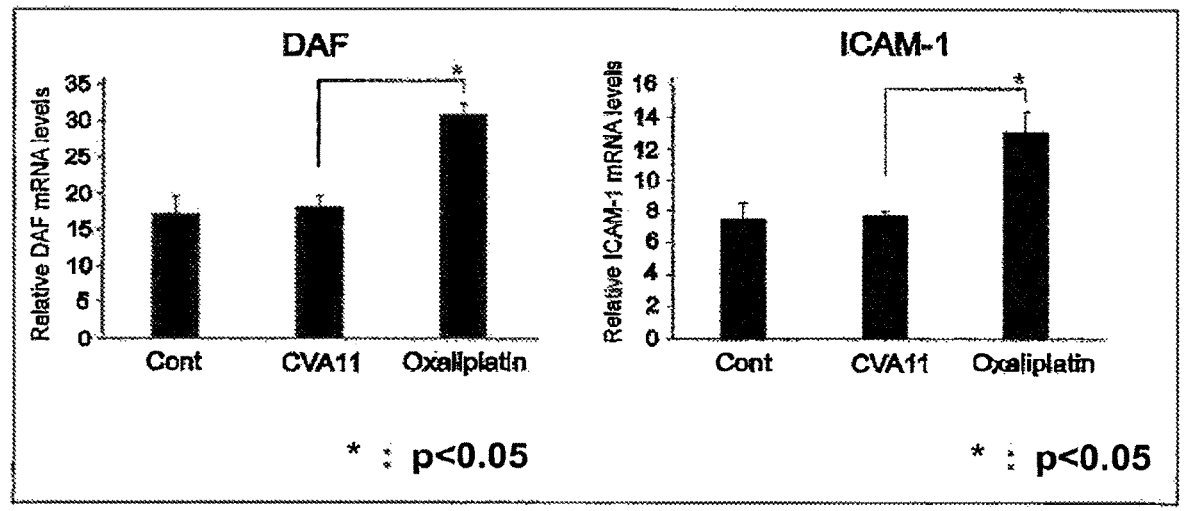
FIG. 3 shows an effect of oxaliplatin for increasing the expression of virus receptors.

FIG. 3 shows the results of the real-time PCR.

In the oxaliplatin-resistant colon cancer cell line (WiDr), the addition of oxaliplatin significantly increased the expressions of DAF and ICAM-1 which are virus receptors. In contrast, the addition of CVA11 did not increase the expressions of DAF and ICAM-1. Some virus receptors are known to affect virus proliferation, and thus it was considered from this result that the reason why the antitumor effect of CVA11 on WiDr was increased by the pretreatment with oxaliplatin is that DAF and ICAM-1 were involved in virus proliferation and CVA11 viruses were proliferated.

Example 4 Antitumor Effect In Vivo of Combination of Oxaliplatin and CVA11, 1

(1) Method

The antitumor effect of CVA11 on cancer cells confirmed in Example 1 was examined by using nude mice bearing oxaliplatin-resistant colon cancer cell line WiDr. WiDr was washed with PBS and suspended in OPTI-MEM I at $5.0 \times 10^7$ cells/mL. 100 µl of the suspension containing WiDr was injected subcutaneously with a 27 G needle into the right flank of BALB/c nude mice of 6-8 weeks old. The mice were divided into the four groups: 1) untreated group, 2) oxaliplatin only administration group, 3) CVA11 only administration group, and 4) oxaliplatin and subsequent CVA11 administration group. 100 µg of oxaliplatin was administered intraperitoneally to the mice on day 1. CVA11 was injected locally into the tumor under the skin at $5 \times 10^7$ plaque forming units (PFU) on days 2, 4, 6, 8, and 10. For the untreated group, OPTI-MEM I not containing CVA11 was administered into the right flank in the same amount as that for the CVA11 administration group. After the administration of CVA11, the tumor volume and body weight were measured for each group. The tumor volume was calculated by major axis×minor axis×minor axis×0.5. The test was conducted using 5 mice in each group, and the t-test was used as the test.

(2) Result

Figure 4:
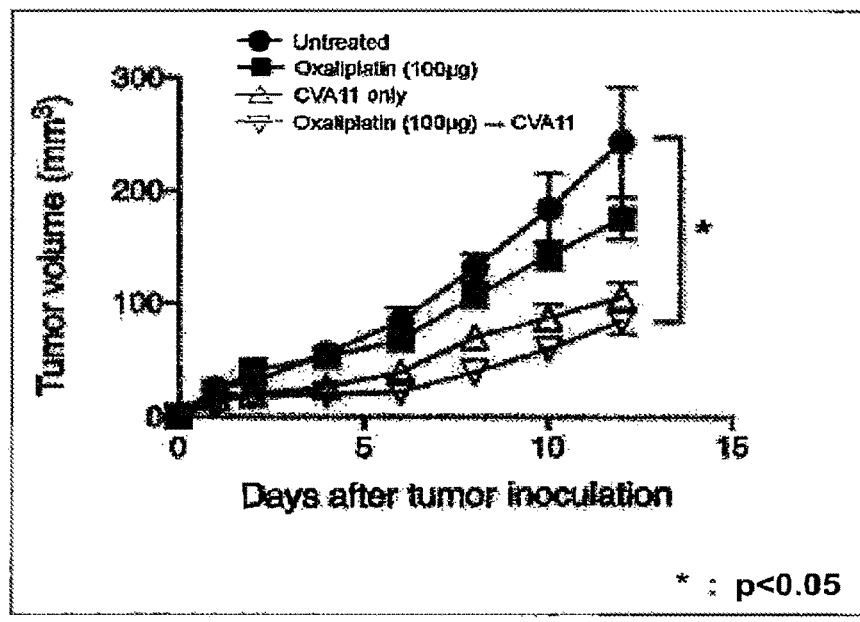
FIG. 4 shows an antitumor effect (suppression of increase in tumor volume) in human colon cancer-bearing mice.

FIG. 4 shows the tumor volumes in the untreated group and those in the oxaliplatin only administration group, the CVA11 only administration group, and the oxaliplatin and subsequent CVA11 administration group (combined administration group). In the mice to which oxaliplatin was administered and then CVA11 was administered, an increase in the tumor volume was significantly suppressed as compared with the untreated group. Further, in the combined administration group, the increase in the tumor volume was significantly suppressed even as compared with the oxaliplatin only administration group and the CVA11 only administration group, and thus a potent antitumor effect was confirmed.

Figure 5:
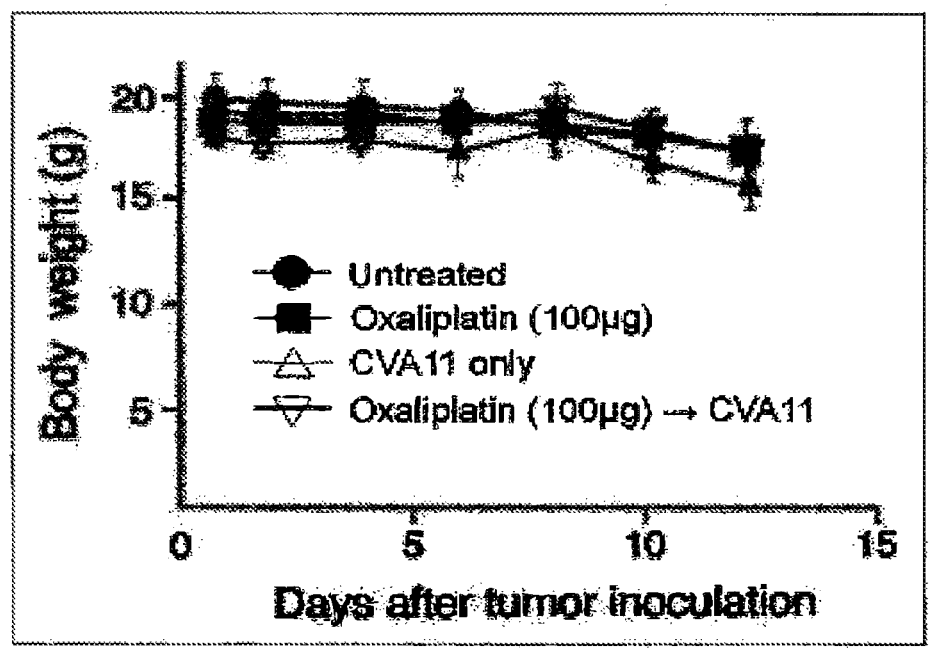
FIG. 5 shows occurrence of adverse events (suppression of body weight loss) in human colon cancer-bearing mice.

FIG. 5 shows changes in the body weight in these four groups. As a result, no significant weight loss was observed in the mice to which oxaliplatin only was administered, the mice to which CVA11 only was administered, and the mice to which oxaliplatin was administered and then CVA11 was administered, as compared with the mice in the untreated group. Since the weight loss at this time point suggests an adverse event, the fact that the weight loss was not observed indicates that the adverse event was not observed even in the mice to which oxaliplatin was administered and then CVA11 was administered and that the antitumor therapy of the present invention is highly safe.

Example 5 Antitumor Effect In Vivo of Combination of Oxaliplatin and CVA11, 2

(1) Method

The percent survival of cancer-bearing nude mice inoculated subcutaneously with oxaliplatin-resistant colon cancer cell line WiDr in Example 4 was compared, and the pathological tissues of tumors on day 40 after subcutaneous inoculation were evaluated by H.E. (hematoxylin eosin) staining.

(2) Result

Figure 6:
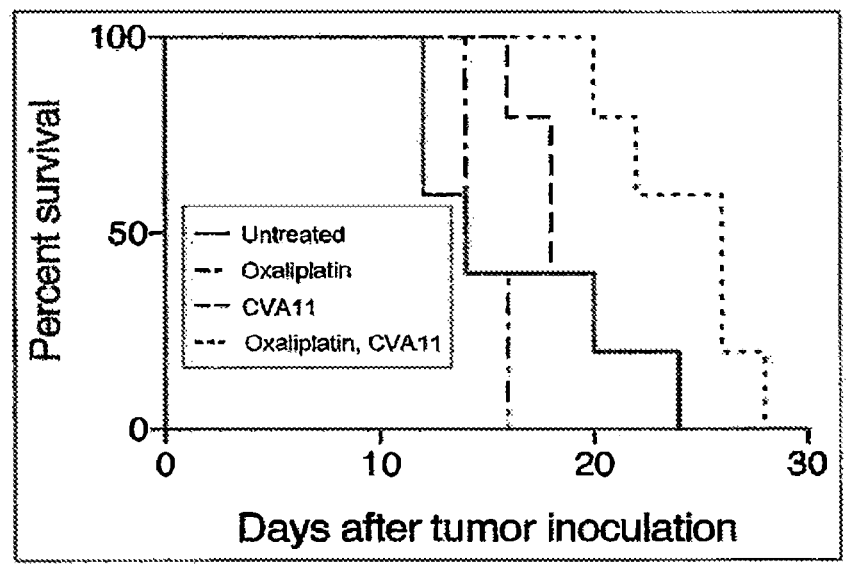
FIG. 6 shows an antitumor effect (percent survival) in human colon cancer-bearing mice.
Figure 7:
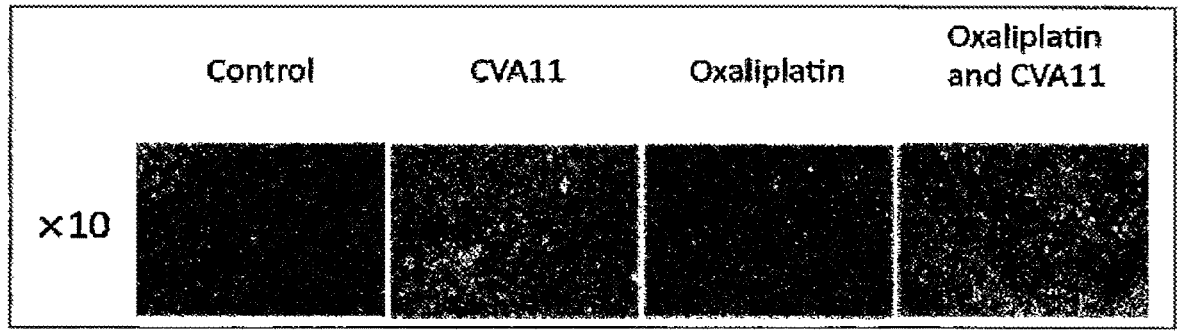
FIG. 7 shows an antitumor effect in human colon cancer-bearing mice (tumor histological images). Arrows indicate dead cells.

FIG. 6 shows data comparing the percent survival of the cancer bearing nude mice. The percent survival of the mice to which oxaliplatin was administered and then CVA11 was administered was improved as compared with the mice in the untreated group, those in the oxaliplatin only administration group, and those in the CVA11 only administration group. In addition, FIG. 7 shows the pathological tissues (H.E. staining) of tumor tissues. Among the pathological tissues of tumors stained with H.E., the pathological tissue of the mice to which oxaliplatin was administered and then CVA11 was administered showed cell death in a wider area. It was confirmed also from the results of the percent survival and the observation of the pathological tissues that the present invention provides a potent antitumor effect.

Example 6 Antitumor Effect of Combination of Oxaliplatin and CVB3

(1) Method (a) Preparation of CVB3

CVB3 was obtained from the National Institute of Infectious Diseases. CVB3 was proliferated using HELA cells (purchased from ATCC). CVA11 (seeding amount: MOI=0.1 to 1.0) was incubated for 1 hour on HELA cells (about $2 \times 10^6$ cells/mL) subcultured with 10 ml of Dulbecco's modified Eagle medium (DMEM) (manufactured by Sigma-Aldrich), then the medium was replaced with DMEM, and the resultant was allowed to stand until a cytopathic effect was observed. After removing the medium, 1 mL of OPTI-MEM I was added to the culture dish, and the cells were detached and collected using a cell scraper. It should be noted that CVB3 and HELA cells were cultured in an incubator at 37° C., 5% $CO_2$. After freezing and thawing of the collected HELA cells were repeated three times using liquid nitrogen, the supernatant was collected by centrifugation at 3000 rpm for 15 minutes at 4° C. The collected supernatant (virus solution) was stored at −80° C.

(b) Calculation of MOI

The MOI was calculated in the same manner as in Example 1(1)(b).

(c) Study on Antitumor Effect of CVB3 Using Crystal Violet Method

CVB3 was used as the virus. The study was performed in the same manner as in Example 1(1)(c) except that the multiplicity of infection (MOI) of CVB3 was set to 0 (no addition), 0.001, 0.01, or 0.1, and the addition amount of oxaliplatin was set to 0 µM (no addition), 0.5 µM, 1 µM, or 5 µM.

(2) Result

Figure 8:
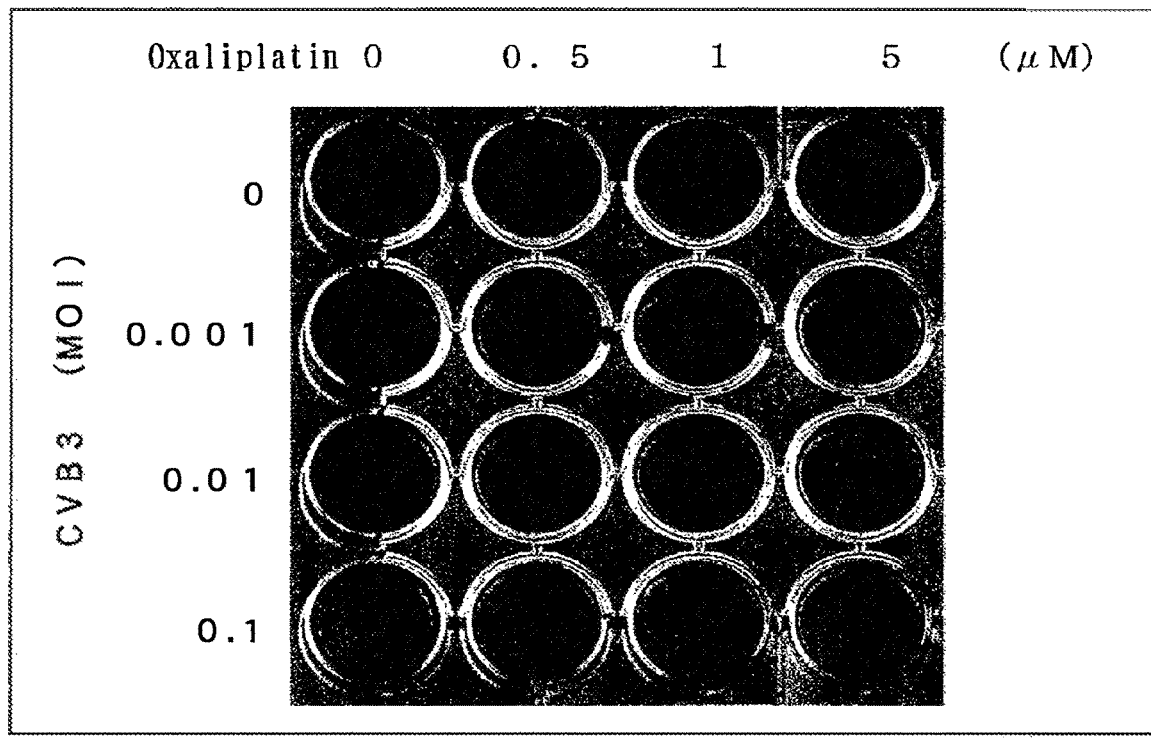
FIG. 8 shows cytotoxicity of the combination of oxaliplatin and CVB3 against oxaliplatin-resistant colon cancer cell line (WiDr).

FIG. 8 shows the results by the crystal violet method. No antitumor effect was observed in the group to which oxaliplatin only was added (the row of MOI of CVB3 of 0 in FIG. 8) and the group to which CVB3 only was added (the column of OXA of 0 in FIG. 8). In contrast, in the group to which oxaliplatin was added and then CVA11 was added (group in the frame), a potent antitumor effect was observed depending on the MOI and the addition amount of oxaliplatin.

Example 7 Effect of Oxaliplatin for Promoting Proliferation of CVB3

(1) Method

CVB3 was prepared in the same manner as in Example 6(1)(a). In addition, the MOI was calculated in the same manner as in Example 1(1)(b).

The cultured oxaliplatin-resistant colon cancer cell line (WiDr) was suspended in DMEM medium at $3\times10^6$ cells/mL. To each well of a 96-well plate, 100 µl of the obtained cell suspension was dispensed and the cells were seeded at $3\times10^5$ cells/well. The plate was allowed to stand for about 8 hours at 37° C., 5% $CO_2$, and then oxaliplatin was added thereto at a final concentration of (no addition), 0.5, or 1.0 µM. Subsequently, the plate was allowed to stand for about 12 hours at 37° C., 5% $CO_2$, and then CVB3 was added thereto at a MOI of 0.01. After the plate was allowed to stand for about 30 hours at 37° C., 5% $CO_2$, multiplicity of infection of the virus was measured by the method as described in Example 1(1)(b). The following three groups were prepared and compared: 1: oxaliplatin was not added, 2: oxaliplatin was added at 0.5 µM, and 3: oxaliplatin was added at 1.0 µM. The test was conducted six times, and the t-test was used as the test.

(2) Result

Figure 9:
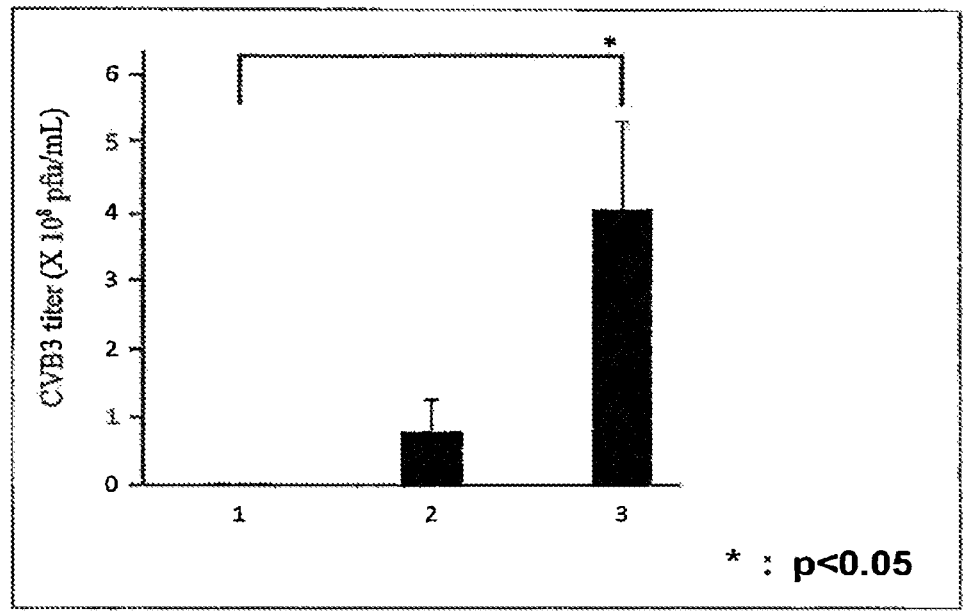
FIG. 9 shows that oxaliplatin promotes the proliferation of CVB3. 1: oxaliplatin was not added, 2: oxaliplatin was added at 0.5 µM, and 3: oxaliplatin was added at 1.0 µM.

FIG. 9 shows the results of virus titers of CVB3. In the group to which oxaliplatin was added, an increase in CVB3 virus load was observed. In particular, a significant increase was observed when oxaliplatin was added at 1 µM. It was confirmed from this result that oxaliplatin promotes the proliferation of not only CVA11 but also CVB3.

Example 8 Effect of Oxaliplatin for Promoting Proliferation of AAV (1) Method
(a) Preparation of AAV pAAV-CMV Vector (manufactured by Takara Bio Co., Ltd.) was used as AAV. pAAV-CMV Vector was prepared using AAVpro (registered trademark) Helper Free System (manufactured by Takara Bio Co., Ltd.). The collected supernatant (virus solution) was stored at −80° C.
(b) Calculation of MOI The MOI was calculated in the same manner as in Example 1(1)(b).
(c) Addition of Oxaliplatin The cultured oxaliplatin-resistant colon cancer cell line (WiDr) was suspended in DMEM medium at $3\times10^6$ cells/well. To each well of a 96-well plate, 100 µl of the obtained cell suspension was dispensed and the cells were seeded at $3\times10^5$ cells/well. The plate was allowed to stand for about 8 hours at 37° C., 5% $CO_2$, and then oxaliplatin was added thereto at a final concentration of (no addition), 0.25, 0.5, 1.0, or 2.5 µM. Subsequently, the plate was allowed to stand for about 24 hours at 37° C., 5% $CO_2$, and then AAV was added thereto at a MOI of 0.01. After the plate was allowed to stand for about 30 hours at 37° C., 5% $CO_2$, virus copy numbers were measured using AAVpro (registered trademark) Titration Kit (for Real Time PCR) Ver.2 (manufactured by Takara Bio Co., Ltd.). The t-test was used as the test.

(2) Result

Figure 10:
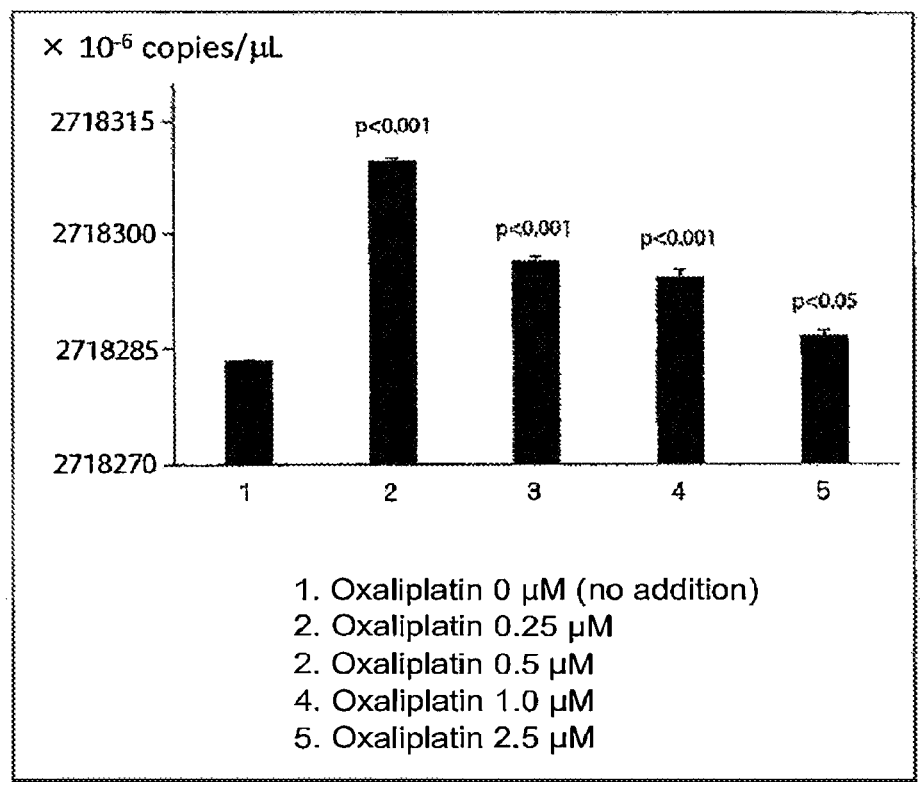
FIG. 10 shows that oxaliplatin promotes the proliferation of AAV.

FIG. 10 shows the results of the copy numbers of AAV. In the group to which oxaliplatin was added, a significant, increase in the copy number of AAV was observed. In particular, a remarkable increase was observed when the addition amount of oxaliplatin renged from 0.25 to 1.0 µM. It was confirmed from this result that oxaliplatin promotes the proliferation of AAV.

Example 9 Effect of SN-38 for Promoting Proliferation of CVA11

(1) Method

The preparation of CVA11 and the calculation of MOI were performed in the same manner as in Example 1(1)(a) and (b).

The cultured oxaliplatin-resistant colon cancer cell line (WiDr) was suspended in DMEM medium at $3\times10^6$ cells/mL. To each well of a 96-well plate, 100 µl of the obtained cell suspension was dispensed and the cells were seeded at $3\times10^5$ cells/well. The plate was allowed to stand for about 8 hours at 37° C., 5% $CO_2$, and then SN-38 was added thereto at a final concentration of 0 (no addition), 1.0, 5.0, or 50 µM. Subsequently, the plates was allowed to stand for about 12 hours at 37° C., 5% $CO_2$, and then CVA11 was added thereto at a MOI of 0.01. After the plate was allowed to stand for about 30 hours at 37° C., 5% $CO_2$, multiplicity of infection of the virus was measured by the method as described in Example 1(1)(b). The following four groups were prepared and compared: 1: SN-38 was not added, 2: SN-38 was added at 1.0 µM, 3: SN-38 was added at 5.0 µM, and 4: SN-38 was added at 50 µM. The test was conducted six times, and the t-test was used as the test.

(2) Result

Figure 11:
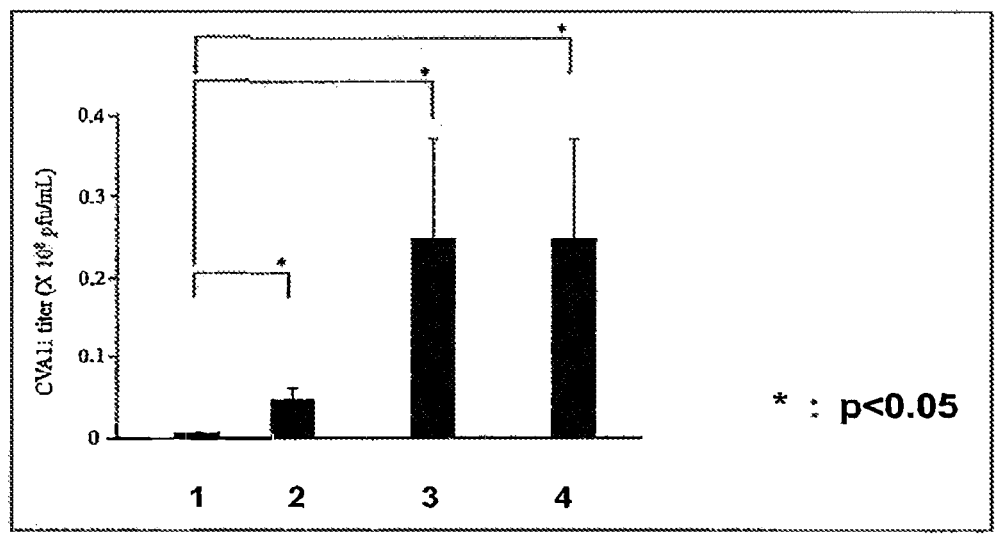
FIG. 11 shows that SN-38 promotes the proliferation of CVA11. 1: SN-38 was not added, 2: SN-38 was added at 1.0 µM, 3: SN-38 was added at 5.0 µM, and 4: SN-38 was added at 50 µM.

FIG. 11 shows the results of virus titers of CVA11 at the time of addition of SN-38. In the group to which SN-38 was added, a significant increase in CVA11 virus load was observed. It was confirmed that not only oxaliplatin but also SN-38 promotes the proliferation of CVA11.

Example 10 Effect of 5-FU for Promoting Proliferation of Cva11

(1) Method

The preparation of CVA11 and the calculation of MOI were performed in the same manner as in Example 1(1)(a) and (b).

The cultured oxaliplatin-resistant colon cancer cell line (WiDr) was suspended in DMEM medium at $3\times10^6$ cells/mL. To each well of a 96-well plate, 100 µl of the obtained cell suspension was dispensed and the cells were seeded at $3\times10^5$ cells/well. The plate was allowed to stand for about 8 hours at 37° C., 5% $CO_2$, and then 5-FU was added thereto at a final concentration of 0 (no addition) or 50 µM. Subsequently, the plate was allowed to stand for about 12 hours at 37° C., 5% $CO_2$, and then CVA11 was added thereto at a MOT of 0.01. After the plate was allowed to stand for about 30 hours at 37° C., 50 $CO_2$, multiplicity of infection of the virus was measured by the method as described in Example 1(1)(b). The following two groups were prepared and compared: 1: 5-FU was not added, and 2: 5-FU was added at 50 µM. The test was conducted six times, and the t-test was used as the test.

(2) Result

Figure 12:
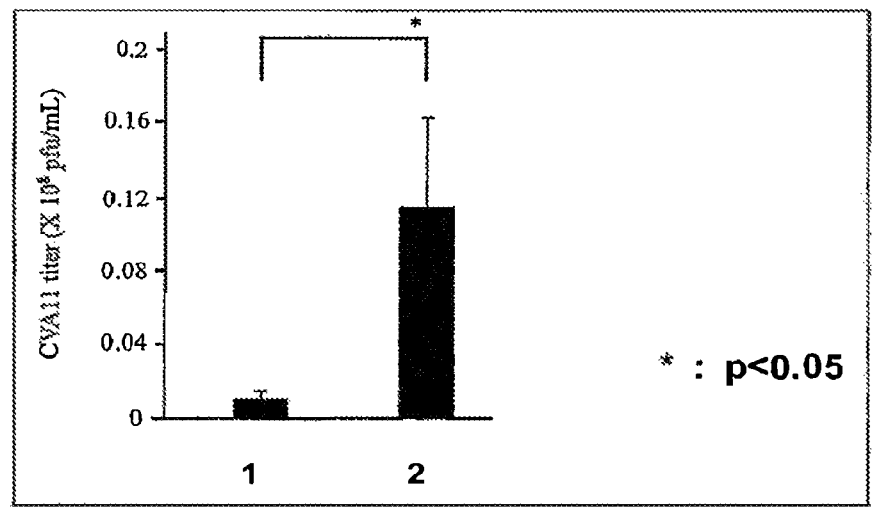
FIG. 12 shows that 5-FU promotes the proliferation of CVA11. 1: 5-FU was not added, and 2: 5-FU was added at 50 µM.

FIG. 12 shows the results of virus titers of CVA11 at the time of addition of 5-FU. In the group to which 5-FU was added, a significant increase in CVA11 virus load was observed. It was confirmed that not only oxaliplatin and SN-38 but also 5-FU promotes the proliferation of CVA11.

Example 11 Antitumor Effect of Combination of Oxaliplatin and CVA11 Against Brain Tumor Cell Line U-87

(1) Method
(a) Preparation of CVA11

The preparation of CVA11 was performed in the same manner as in Example 1(1)(a).
(b) Calculation of MOI The MOI was calculated in the same manner as in Example 1(1)(b) except that brain tumor cell line U-87 was used instead of the oxaliplatin-resistant colon cancer cell line (WiDr).
(c) Study on Antitumor Effect Using Crystal Violet Method The antitumor effect (cytotoxicity) of the combination of CVA11 and oxaliplatin against brain tumor cell line U-87 was evaluated by the crystal violet method.

The brain tumor cell line U-87 was seeded in a 24-well plate at a density ($3\times10^4$ cells/well) becoming confluent after 72 hours. Then, oxaliplatin was added thereto at 0 (no addition) or 50 µM. For the preparation of a diluted solution of CVA11, CVA11 was diluted with OPTI-MEM I so as to accomplish a MOI of 0.001. After about 6 hours, the medium was removed from the plate, 200 µl of the diluted solution of CVA11 was added to each well, and the plate was maintained for 1 hour at 37° C., 5% $CO_2$. Next, the diluted solution of CVA11 was removed, and 1 ml of cell culture medium was added to each well, followed by culturing for 72 hours. After 72 hours, the cells were washed gently with phosphate buffered saline (PBS), 300 µL of PBS containing 0.5% glutaraldehyde was added to each well, and then the plate was allowed to stand for 15 minutes at room temperature to fix viable adherent cells. Thereafter, the PBS containing glutaraldehyde was removed, washing with PBS was performed, and then 300 µL of sterile water containing 2% ethanol and 0.1% crystal violet was added to each well, followed by standing for 10 minutes at room temperature, to thereby stain viable cells. Each well of the plate after staining was washed twice with 500 µL of sterile water, and staining was recorded using a scanner to confirm the antitumor effect.

(2) Result

Figure 13:
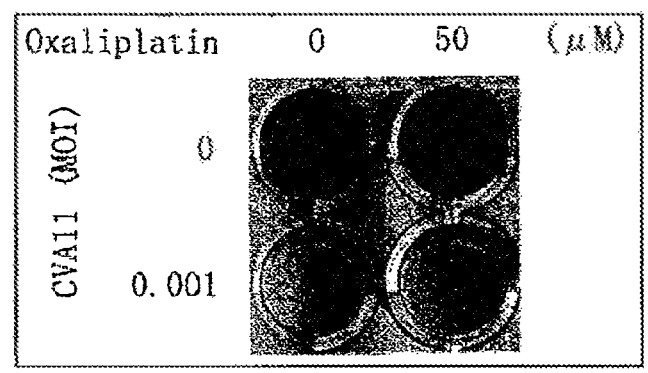
FIG. 13 shows cytotoxicity against brain tumor cells U-87.

FIG. 13 shows the results by the crystal violet method. Even in the group to which CVA11 only was added, an antitumor effect was confirmed, but in the group in which CVA11 was used in combination with 50 µM oxaliplatin, the enhancement of the antitumor effect was confirmed. This indicated that the antitumor therapy is also effective for brain tumor, which is a cancer type other than colon cancer.

Comparative Example 1 Comparison of Antitumor Effect of Combination of CVA11 and Oxaliplatin and that of Combination of CVA11 and Cisplatin (1) Method
(a) Preparation of CVA11 and Calculation of MOI The preparation of CVA11 and the calculation of MOI were performed in the same manner as in Example 1(1)(a) and (b).

(c) Comparison of Antitumor Effects Using Crystal Violet Method

The study was performed in the same manner as in Example 1(1)(c) except that the MOI of CVA11 was set to 0 (no addition), 0.001, 0.01, or 0.1, and the addition amount of oxaliplatin or cisplatin was 0 µM (no addition), 0.5 µM, 1 µM, or 5 µM.

(2) Result

Figure 14:
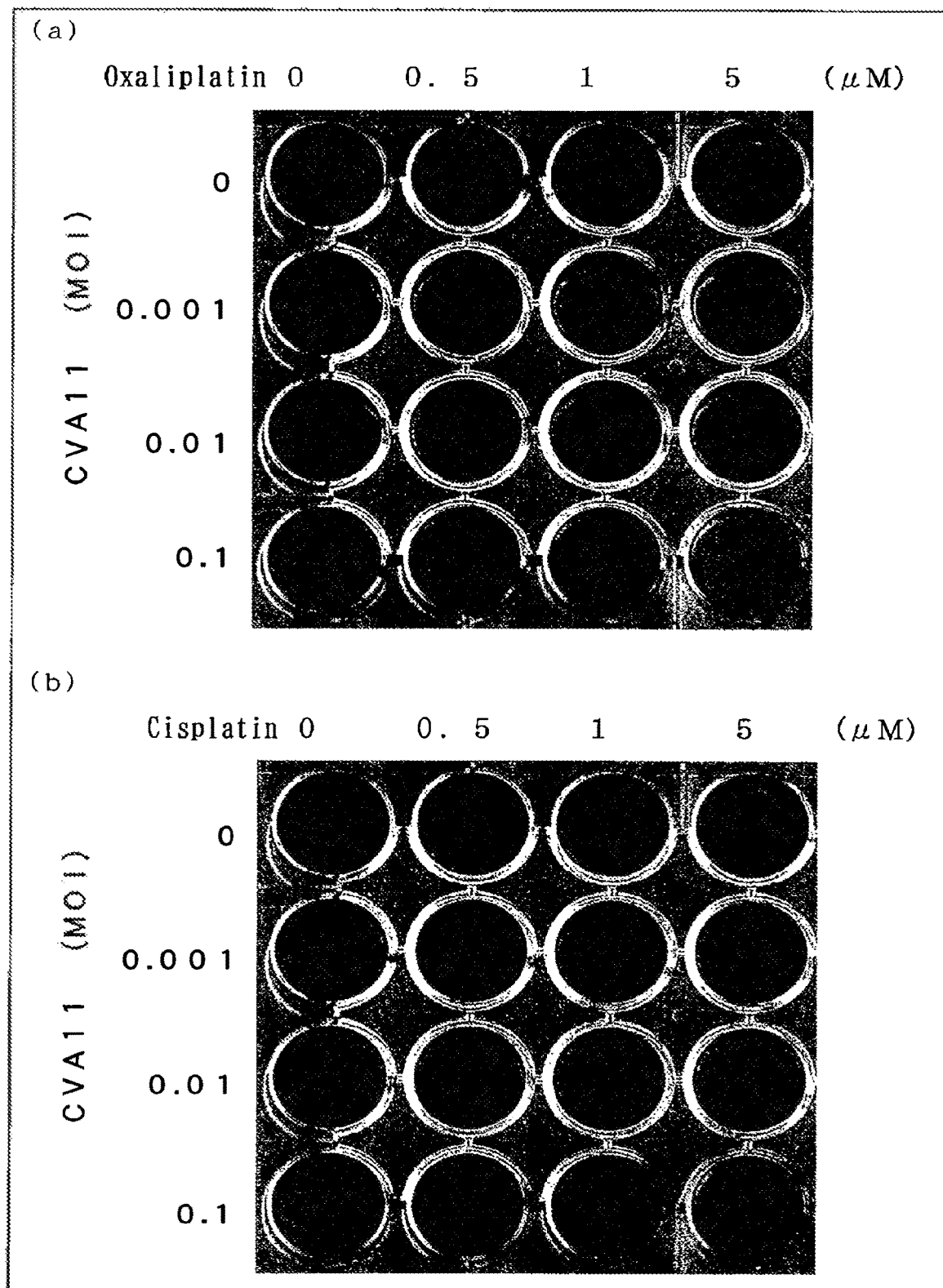
FIG. 14 shows the comparison of cytotoxicity of the combination of oxaliplatin and CVA11 and that of the combination of cisplatin and CVA11. (a) shows cytotoxicity of the combination of oxaliplatin and CVA11. (b) shows cytotoxicity of the combination of cisplatin and CVA11.

FIG. 14(a) shows the results by the crystal violet method at the time of addition of oxaliplatin, and FIG. 14(b) shows the results by the crystal violet method at the time of addition of cisplatin. The combination of CVA11 and oxaliplatin showed a more potent antitumor effect as compared with the combination of CVA11 and cisplatin. This result indicated that the combination of the oncolytic virus CVA11 and oxaliplatin is particularly useful as compared with the combination of CVA11 and cisplatin reported in the publication (WO 2013-157648).

Comparative Example 2 Effect of Cisplatin for Promoting Proliferation of CVB3

(1) Method

The study was performed in the same manner as in Example 7 except that cisplatin was used instead of oxaliplatin. The following three groups ware prepared and compared: 1: cisplatin was not added, 2: cisplatin was added at 0.5 µM, and 3: cisplatin was added at 1.0 µM.

(2) Result

Figure 15:
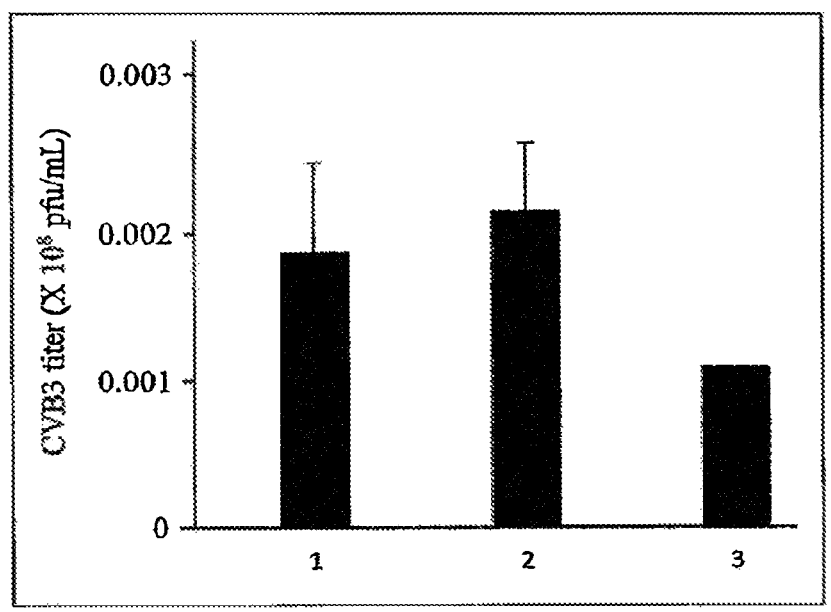
FIG. 15 shows that the addition of cisplatin does not promote the proliferation of CVB3.

FIG. 15 shows the results of virus titers of CVB3. Unlike the case where oxaliplatin was added (FIG. 9), even when cisplatin was added, no increase in CVB3 virus load was observed. This result indicated that, when combined with an oncolytic virus, oxaliplatin is more useful as compared with cisplatin.

The invention claimed is:

1. A method for enhancing an antitumor effect of a coxsackievirus, the method comprising:
   administering oxaliplatin and the coxsackievirus to a subject in need thereof.

2. The method according to claim 1, wherein the antitumor effect is an antitumor effect against oxaliplatin-resistant cancer.

3. A method for promoting proliferation of a coxsackievirus, the method comprising:
   culturing the coxsackievirus in the presence of oxaliplatin.

4. A method for enhancing an expression of a virus receptor of a cancer cell, the method comprising:
   administering oxaliplatin,
   wherein the virus receptor is DAF, ICAM-1, or a combination thereof.

5. A method for treating oxaliplatin resistant cancer, the method comprising:
   administering an antitumor agent comprising a combination of oxaliplatin and an antimetabolite and a coxsackievirus to a patient having oxaliplatin-resistant cancer.

6. The method according to claim 1, wherein the coxsackievirus is coxsackievirus A11 or coxsackie virus B3.

7. The method according to claim 3, wherein the coxsackievirus is coxsackievirus A11 or coxsackievirus B3.

8. The method according to claim 5, wherein the coxsackievirus is coxsackievirus A11 or coxsackievirus B3.

* * * * *

SEQUENCE LISTING

<160> NUMBER OF SEQ ID NOS: 3

<210> SEQ ID NO 1
<211> LENGTH: 7453
<212> TYPE: DNA
<213> ORGANISM: Coxsackievirus A11

<400> SEQUENCE: 1

```
ttaaaacagc tgtggggttg ttcccacccc agaggcccac gtggcggcta gtactccggt      60
atcacggtac ccttgtacgc ctgttttata ctccctcccc cgtaacttag aagcaatcaa     120
atcaagttca ataggagggg gtacaaacca gtaccaccac gaacgagcac ttctgtttcc     180
ccggtgaagt tgcatagact gttaccacgg ttgaaagcga ccgatccgtt atccgctcat     240
gtacttcgag aagcctagta cctccttgga atcttcgatg cgttgcgctc agcactcaac     300
cccggagtgt agcttaggct gatgagtctg gacagccctc accggcgacg gtggtccagg     360
ctgcgttggc ggcctacctg tggcccaaag ccacaggacg ctagttgtga acaaggtgtg     420
aagagcctat tgagctacat gagagtcctc cggcccctga atgcggctaa tcctaaccac     480
ggagcaggcg atcgcaaacc agcaattagc ctgtcgtaac gcgaaagtct gtggcggaac     540
cgactacttt gggtgaccgt gtttctctta tttttattca tggctgctta tggtgacaat     600
```

```
catagattgt tatcataaag cgagttggat tggccatccg gtaaaagtca agtatatcat    660
ttacttgttt gtaggattta ttcctttgaa cgtccattta ctcaatctta tcagagtcac   720
attactagta agatctcact atcacaatgg gagctcaagt atcatctcag aaagtgggtg   780
cccatgaaaa caccaatgtg gccaccggtg ggtcaactgt aaactacact actattaatt   840
actacaaaga ctcagctagt aacgctgctt ctaaacagga cttctcccag acccatcaa    900
aatttactga gcctgttaaa gacatcatgc tcaagtcagc ccctgctcta aactcaccca   960
atattgaggc atgcgggtat agtgataggg tgatgcagtt gactcttggg aattccacca  1020
ttactacaca ggaagcagcc aattcagtgg tagcatacgg tgagtggccg tcttatttgt  1080
cagacaaaga ggctaacccg gttgaccagc caacggagcc cgaagtgtct gcatgcagat  1140
tctacacgtt agatacagtc acgtggagta agagttcaaa aggatggtgg tggaaactac  1200
cggatgcact caaagacatg gggttgttcg ggcaaaacat gtactaccac tacctgggcc  1260
gttcgggcta cactgtgcat gtgcaatgta atgcatccaa gttccaccag ggcgctttgg  1320
gcgttttcgc cattccagag tactgtatgg cctgcaacac tgatgctaag accaactatg  1380
ttagctatgt acaagcaaac ccaggtgagg ctggtggagt cttttaccgac atgtacaatc  1440
ccagttcaga aacaactggg gcacgaaagt ttgcagcggt ggattacctg cttggttgtg  1500
gagtgttggc tggtaacgct ttcgtcttcc cccaccaaat catcaatctc cgcaccaaca  1560
actgtgctac actagttta ccttacgtga actcaatggc aattgattgt atggcaaaac  1620
acaacaattg gggaatagca atactacctc ttgctgagct ggactttgct gaggcgtcat  1680
ctcctgaaat ccccataacc atcacaatcg caccgatgtg ttgtgagttc aatggactga  1740
ggaatttgac tagtccagct aaacagggcc taccagtaat gaatgtacct ggtagtaatc  1800
agttcttatc atctgacaat ttccaatcac cgtgtgcctt acctgagttt gacgtaacac  1860
caccgataca cattccaggt gaagttagga acatgatgga gcttgccgaa atagatacct  1920
taattccaat ggatctcagc gaatccaaga aaaacacaat gggaatgtac agagttgagt  1980
tagggtctgg caagtcacta tctaaaccca tactgtgtct tagcttgagt ccagctagtg  2040
aacaacgttt agggtacacc atgttgggag agattctgaa ttactataca cactggagtg  2100
ggtctttgaa attcaccttt ctgttctgtg ggagcatgat ggcaacaggc aagattttaa  2160
tatcgtatgc accaccaggt gcgaaaccac ctacaaccag aagggaggcc atgcttggca  2220
cacacgtgat ttgggacatt ggacttcagt catccgcgac catggtcgtg ccttggatca  2280
gtaacgttat gtaccggagg tgtgtgaagg atgactttac tgaaggtgga tatatatcaa  2340
tgttctacca gactaaaatc gtggtgcctc tatcaacacc caccacaatg acactactca  2400
gctttgtgtc agcatgcaac gactttaccg tgcggttgtt gagagacacc acccacatct  2460
cccaaacaac gaaaatcaac actcaagggc caatagaaga aatcatctca actgttgcca  2520
gtaacgcgtt ggcgctcagt caacccaagc cagtggacaa ctctgtacaa aacacccaac  2580
aaagtgctcc agtgcatagc caggaggtgc cagcattgac cgcagtggag acaggggcga  2640
caagtgatgt ggttccatct gacctaattc agactagaca cgtattgaat gttaaatcca  2700
ggtctgaatc caccatcgag tcattttttg caagagctgc atgtgtaacc attatgcagg  2760
tggacaattt caacgcaacc tctgtggaag acaaaagaaa gttgtttgct aaatgggcaa  2820
tcacctacac tgataccgtc cagctgagac ggaaattaga gttttcact tattctagat  2880
ttgacttaga gatgacttt gtgctaactg agagatacta ctcccaaagc tcagggcatg  2940
ctagatctca ggtgtaccaa attatgtatg ttccaccagg ggcacccacg cctagtgcat  3000
```

```
gggacgacta cacatggcaa acatcctcca acccatccat tttctttacc accggcaatg    3060
caccaccgcg catttcaatt ccatttgttg aatcgccaa tgcatactca cacttttatg     3120
atggctttag tagagtacct ttggagggag aaacaacaga cacaggagac gcttactacg    3180
ggctcacttc aataaacgat tttggtacac ttgcagtcag ggtagttaat gactacaacc    3240
cagccagggt ggagacaagg attagagtat acatgaagcc caaacatgtg agagtctggt   3300
gcccgcgacc tccaagagcg gtaagctaca gaggacctgg agtcgacctc ctatcaacat    3360
cagtaacacc tttatccaaa catgacctag cgacatacgg gtttggccac cagaacaaag   3420
cagtttacac agcagggtat aagatttgca actaccacct agctacccag gaagacatgc   3480
agaacgcagt gagcatcatg tggaatagag atctcttgat cgccgagtca aaggctcagg   3540
gtattgactc aatagccagg tgtaattgca atacaggtgt atattattgt gagtctagga   3600
gaaagtacta cccaatttcc tttgtgggg caaccttcca atacatggag gccaacgatt    3660
actaccctgc aaggtatcaa tcacacatgc taatagggca cggttttgca tcaccaggcg   3720
attgtggtgg cattctcaga tgtcaacatg gagtcatagg attgataact gccggggcg     3780
agggcctagt tgcattctcg gacatcagag atttatatgc atatgaagag gaagccatgg    3840
agcaaggaat ctcgaactac attgagtcac taggggctgc atttggcagc gggtttactc    3900
aacagattgg agataaaata tcagagctta ccagtatggt caccagcacg atcactgaaa    3960
aattacttaa aaacttgatc aaaattatct cgtctcttgt catcatcacc agaaattatg    4020
aggacaccac cacggtgctc gccaccttgg cactcctcgg ctgtgacgtt tctccatggc   4080
aatggctgaa gaagaaagca tgtgacatct tagaaatccc ctatgttgta aggcaaggtg    4140
atagttggct gaagaaattc accgaggcgt gcaacgcagc taaaggcctg gagtgggtgt    4200
caaacaagat ttctaagttt atagactggc tcaaggaaag gatcattcca caagctagag   4260
ataaacttga gttcgtcact aagcttaagc agctggagat gctagagaat cagattgcta    4320
ccatacacca atcttgtccc agccaagagc atcaggagat tctgttcaat aatgtacgtt    4380
ggttgtcgat ccaatccaaa agatttgcac ctttgtatgc acttgaggcc aaaagaatcc    4440
aaaagttgga acacaccatt aacaactaca tacagttcaa gagcaaacac cgtattgaac   4500
cagtatgttt actagtgcat ggtagtccag gaacaggcaa gtcagttgca acaaatttaa    4560
tagctagagc aattgctgag aaagagaaca cttcaacata ctcgctacca cccgacccttt   4620
cacactttga tggwtacaaa cagcagggag tggtaatcat ggacgacctc aatcagaacc    4680
ctgatggggc tgacatgaaa ctattctgtc agatggtgtc tacagttgaa tttatcccac    4740
caatggcatc tttagaagag aaaggcattc tgtttacgtc caactatgtg ctagcttcca   4800
ccaactccag tcggattgca ccacctactg tagcccatag tgatgcacta gccaggaggt    4860
ttgcctttga catagatatt caggtcatga atgagtactc cagagatgga aagcttaata    4920
tggcaatggc tacggagatg tgcaagaact gccaccaacc agcaaacttc aagagatgct   4980
gtcctctggt gtgcggaaaa gcaattcagt taatggataa gtcatcaaga gtcaggtata    5040
gtgtggatca gattactact atgatcatca atgaaaggaa tagaagatca aatattggca    5100
attgtatgga agcactcttc caaggaccac tccagtacaa agacttgaaa attgacatta    5160
aaacaacacc acccccagag tgcatcaatg atttgctcca ggcagttgac tcccaagagg   5220
ttagggacta ttgtgagaag aaagggtgga ttgtcaatat caccagtcaa gtccaaactg    5280
aaaggaacat caatagagct atgacaattc tgcaagctgt cacaacattt gctgcgcgtgg   5340
ccggagttgt gtacgtcatg tacaaacttt tcgctggata tcaaggagct acaccggcc     5400
```

```
tcccgaacaa aagacctagc gtacctacca ttagaactgc taaggtgcag ggtccaggct    5460
tcgactacgc agtcgcaatg gctaaaagaa acatagttac tgctaccacc agtaagggggg   5520
aatttaccat gctaggagtt catgacaatg tggcgatttt accaactcat gcgtcgcctg    5580
gagagagcat tgtgattgat ggaaaagagg tggagatttt agatgcaaag gctcttgaag    5640
accaagcagg cacaaatctg gaaattacaa ttataacact gaaagaaat gaaaaattca     5700
gagacattag accacacatt cccacacaga ttactgagac taacgatgga gtgctgatcg    5760
tgaacactag taagtatccc aacatgtatg tgcctgttgg tgctgtgacc gaacagggat    5820
atcttaatct cggtgggcgt caaacagctc gtacattaat gtacaatttc ccaactagag    5880
cgggccagtg tggtggagtt gtcacttgca ctggtaaggt catcgggatg catgttggtg    5940
ggaatggttc acatgggttc gcagcggccc taaagcgatc gtatttcact cagagtcaag    6000
gtgagattca gtggataaga ccatcaaaag aagtgggtta ccccatcatt aatgctcctt    6060
ccaagactaa attgaaccct agtgcctttc attatgtgtt tgagggagtc aaagagccag    6120
cagtccttac taagaatgac cctagactaa aaacagattt tgaagaggcc attttctcaa    6180
aatacgtagg gaacaaaatc acggaagtag atgaatacat gaaggaagca gtagaccact    6240
atgcgggaca actactttcc ctagacatca acacagacca gatgtgcctt gaggatgcca    6300
tgtacggcac tgatgggctt gaagctttgg acctcagtac tagtgcaggc tacccttatg    6360
ttgccatggg aaagaaaaag agggacattc taaataaaca aaccagggat accaaggaga    6420
tgcagagatt actcgacacc tatggaatta atctacctct agttacttat gtaaaagatg    6480
aactcaggtc taagacaaaa gtggaacaag gtaaatctag gctaattgaa gcatccagtc    6540
tcaatgattc agttgcaatg agaatggcct ttggtaactt gtatgcagca ttccacaaaa    6600
acccaggtgt ggtgacagga tctgcagttg ggtgcgaccc agacctgttc tggagtaaga    6660
taccagtgct aatggaagaa aaactctttg cttttcgatta cacgggatat gatgcatcac    6720
tcagtcccgc ttggttcgaa gctttgaaaa tggttttgga gaaaattggt tttgagagata   6780
gggtagatta cattgactac ttgaatcact cacaccactt atacaaaaac aaaacttatt    6840
gtgttaaggg tggtatgcca tctggctgct ctggcacttc aatcttcaac tcaatgatca    6900
acaatttgat tatcaggacg ctcttactga aaacctacaa gggcatagat ttagatcacc    6960
taaaaatgat tgcctatggt gatgatgtaa ttgcttctta ccccccatgag gttgacgcta   7020
gtctcctagc ccaatcagga aaagactatg gactaaccat gactccagca gacaagtcag    7080
ctacattcga aacagtcaca tgggagaacg taacattctt gaaaagattc ttcagagcag    7140
atgaaaagta cccctttctg atacatccag tgatgccaat gaaggaaatt catgaatcaa    7200
ttagatggac taaagatccc agaaacaccc aggatcatgt gcgctcatta tgcctattgg    7260
cttggcataa tggcgaagag gagtataaca aatttttagc tagaattaga agtgtgccaa    7320
ttggaagagc attattgctc cctgagtact ctacattgta ccgccgttgg cttgactcat    7380
tctagtaacc ctacctcagt cgaattggat tgggtgatac tgatgtaggg gtaaatttt     7440
cttaattcg gag                                                        7453
```

<210> SEQ ID NO 2  
<211> LENGTH: 7399  
<212> TYPE: DNA  
<213> ORGANISM: Coxsackievirus B3

```
<400> SEQUENCE: 2
ttaaaacagc ctgtgggttg atcccaccca cagggcccat tgggcgctag cactctggta      60
tcacggtacc tttgtgcgcc tgttttatac cccctccccc aactgtaact tagaagtaac     120
acacaccgat caacagtcag cgtggcacac cagccacgtt ttgatcaagc acttctgtta     180
ccccggactg agtatcaata gactgctcac gcggttgaag gagaaagcgt tcgttatccg     240
gccaactact tcgaaaaacc tagtaacacc gtggaagttg cagagtgttt cgctcagcac     300
taccccagtg tagatcaggt cgatgagtca ccgcattccc cacgggcgac cgtggcggtg     360
gctgcgttgg cggcctgccc atggggaaac ccatgggacg ctctaataca gacatggtgc     420
gaagagtcta ttgagctagt tggtagtcct ccggcccctg aatgcggcta atcctaactg     480
cggagcacac accctcaagc cagagggcag tgtgtcgtaa cggcaactc tgcagcggaa      540 ccgactactt tgggtgtccg tgtttcattt tattcctata ctggctgctt atggtgacaa     600
ttgagagatt gttaccatat agctattgga ttggccatcc ggtgaccaat agagctatta     660
tatatctctt tgttgggttt ataccactta gcttgaaaga ggttaaaaca ttacaattca     720
ttgttaagtt gaatacagca aaatgggagc tcaagtatca acgcaaaaga ctggggcaca     780
tgagaccagg ctgaatgcta gcggcaattc catcattcac tacacaaata ttaattatta     840
caaggatgcc gcatccaact cagccaatcg gcaggatttc actcaagacc cgggcaagtt     900
cacagaacca gtaaaagata tcatgattaa atcactacca gctctcaact cccccacagt     960
agaggagtgc ggatacagtg acagggtgag atcaatcaca ttaggtaact ccaccataac    1020
gactcaggaa tgcgccaacg tggtggtggg ctatggagta tggccagatt atctaaagga    1080
tagtgaggca acagcagagg accaaccgac ccaaccagac gttgccacat gtaggttcta    1140
tacccttgac tctgtgcaat ggcagaaaac ctcaccagga tggtggtgga agctgcccga    1200
tgctttgtcg aacttaggac tgtttgggca gaacatgcag taccactact taggccgaac    1260
tgggtatacc gtacatgtgc agtgcaatgc atctaagttc caccaaggat gcttgctagt    1320
agtgtgtgta ccggaagctg agatgggttg cgcaacgcta gacaacaccc catccagtgc    1380
agaattgctg gggggcgata gcgcaaaaga gtttgcggac aaaccggtcg catccgggtc    1440
caacaagttg gtacagaggg tggtgtataa tgcaggcatg ggggtgggtg ttggaaacct    1500
caccattttc ccccaccaat ggatcaacct acgcaccaat aatagtgcta caattgtgat    1560
gccatacacc aacagtgtac ctatggataa catgtttagg cataacaacg tcaccctaat    1620
ggttatccca tttgtaccgc tagattactg ccctgggtcc accacgtacg tcccaattac    1680
ggtcacgata gcccaatgt gtgccgagta caatgggtta cgtttagcag ggcaccaggg    1740
cttaccaacc atgaatactc cggggagctg tcaatttctg acatcagacg acttccaatc    1800
accatccgcc atgccgcaat atgacgtcac accagagatg aggatacctg gtgaggtgaa    1860
aaacttgatg gaaatagctg aggttgactc agttgtccca gtccaaaatg ttggagagaa    1920
ggtcaactct atggaagcat accagatacc tgtgagatcc aatgaaggat ctggaacgca    1980
agtattcggc tttccactgc aaccagggta ctcgagtgtt tttagtcgga cgctcctagg    2040
agagatcttg aactattata cacattggtc aggcagcata aagcttacgt ttatgttctg    2100
tggttcggcc atggctactg gaaaattcct tttggcatac tcaccaccag gtgctggagc    2160
tcctacaaaa agggttgatg ccatgcttgg tactcatgta gtttgggacg tggggctaca    2220
atcaagttgc gtgctgtgta cccctggat aagccaaaca cactaccggt tgttgcttc     2280 agatgagtat accgcagggg gttttattac gtgctggtat caaacaaaca tagtggtccc    2340
```

```
agcggatgcc caaagctcct gttacatcat gtgtttcgtg tcagcatgca atgacttctc    2400
tgtcaggcta ttgaaggaca ctcctttcat ttcgcagcaa aacttttcc agggcccagt     2460 ggaagacgcg ataacagccg ctataggag agttgcggat accgtgggta cagggccaac     2520
caactcagaa gctataccag cactcactgc tgctgagaca ggtcacacgt cacaagtagt    2580
gccgggtgac accatgcaga cacgccacgt taagaactac cattcaaggt ctgagtcaac    2640
catagagaac ttcctatgta ggtcagcatg cgtgtacttt acggagtata aaaactcagg    2700
tgccaagcgg tatgctgaat gggtattaac accacgacaa gcagcacaac ttaggagaaa    2760
gctagaattc tttacctacg tccggttcga cctggagctg acgtttgtca taacaagtac    2820
tcaacagccc tcaaccacac agaaccaaga cgcacagatc ctaacacacc aaattatgta    2880
cgtaccacca ggtggacctg taccagataa agttgattca tacgtgtggc aaacatctac    2940
gaatcccagt gtgttttgga ccgagggaaa cgccccgccg cgcatgtcca taccgttttt    3000
gagcattggc aacgcctatt caaatttcta tgacggatgg tctgaatttt ccaggaacgg    3060
agtttacggc atcaacacgc taaacaacat gggcacgcta tatgcaagac atgtcaacgc    3120
tggaagcacg ggtccaataa aaagcaccat tagaatctac ttcaaaccga agcatgtcaa    3180
agcgtggata cctagaccac ctagactctg ccaatacgag aaggcaaaga acgtgaactt    3240
ccgacccagc ggagttacca ctactaggca aagcatcact acaatgacaa atacgggcgc    3300
atttggacaa caatcagggg cagtgtatgt ggggaactac agggtagtaa atagacatct    3360
agctaccagt gctgactggc aaaactgtgt gtgggaaagt tacaacagag acctcttagt    3420
gagcacgacc acaacacatg gatgtgatat tatagccaga tgtcagtgca caacgggagt    3480
gtacttttgt gcgtccaaaa acaagcacta cccaatttcg tttgaaggac caggtctagt    3540
agaggtccaa gagagtgaat actaccccag gagataccaa tcccatgtgc ttttagcagc    3600
tggattttcc gaaccaggtg actgtggcgg tatcctaagg tgtgagcatg gtgtcattgg    3660
cattgtgacc atgggggtg aaggcgtggt cggctttgca gacatccgtg atctcctgtg    3720
gctggaagat gatgcaatgg aacagggagt gaaggactat gtggaacagc ttggaaatgc    3780
actcggctcc ggctttacta accaaatatg tgagcaagtc aacctcctga agaatcact     3840 agtgggtcaa gactccatct tagagaaatc tctaaaagcc ttagttaaga taatatcagc    3900
cttagtaatt gtggtgagga accacgatga cctgatcact gtgactgcca cactagccct    3960
tatcggttgt acctcgtccc cgtggcggtg gctcaaacag aaggtgtcac aatattacgg    4020
aatccctatg gctgaacgcc aaaacaatag ctggcttaag aaatttactg aaatgacgaa    4080
tgcttgcaag ggtatggaat ggatagctgt caaaattcag aaaattcattg aatggctcaa    4140 agtaaaaatt ttgccagagg tcagggaaaa acacgaattc ctgaacagac ttaaacaact    4200
ccccttatta gaaagtcaga tcgccacaat cgagcagagc gcgccatccc aaagtgacca    4260
ggaacaatta ttttccaatg tccaatactt tgcccactat tgcagaaagt acgctcccct    4320
ctacgcagct gaagcaaaga gggtgttctc ccttgagaag aagatgagca attacataca    4380
gttcaagtcc aaatgccgta ttgaacctgt atgtttgctc ctgcacggga gccctggtgc    4440
cggcaagtcg gtggcaacaa acttaattgg aagtcgcctt gctgagaaac tcaacagctc    4500
agtgtactca ctaccgccag acccagatca cttcgacgga tacaaacagc aggccgtggt    4560
gattatggac gatctatgcc agaaccctga tgggaaagac gtctccttgt tctgccaaat    4620
ggtttccagt gtagattttg taccacccat ggctgccta aagagaaag gcattctgtt     4680 cacctcaccg tttgtcttgg catcgaccaa tgcaggatct attaatgctc caaccgtgtc    4740
```

```
agatagcaga gccttggcaa ggagatttca ctttgacatg aacatcgagg ttatttccat    4800
gtacagtcag aatggcaaga taaacatgcc catgtcagtc aagacttgtg acgatgagtg    4860
ttgcccggtc aattttaaaa agtgctgccc tcttgtgtgt gggaaggcta tacaattcat    4920
tgatagaaga acacaggtca gatactctct agacatgcta gtcaccgaga tgtttaggga    4980
gtacaatcat agacatagcg tggggaccac gcttgaggca ctgttccagg gaccaccagt    5040
atacagagag atcaaaatta gcgttgcacc agagacacca ccaccgcccg ccattgcgga    5100
cctgctcaaa tcggtagaca gtgaggctgt gagggagtac tgcaaagaaa aaggatggtt    5160
ggttcctgag atcaactcca ccctccaaat tgagaaacat gtcagtcggg ctttcatttg    5220
cttacaggca ttgaccacat ttgtgtcagt ggctggaatc atatatataa tatataagct    5280 cttttgcgggt tttcaaggtg cttatacagg agtgcccaac cagaagccca gagtgcctac    5340
cctgaggcaa gcaaaagtgc aaggccctgc ctttgagttc gctgtcgcaa tgatgaaaag    5400
gaactcaagc agggtgaaaa ctgaatatgc cgagtttacc atgctgggca tctatgacag    5460
gtgggccgtt ttgccacgcc acgccaaacc tgggccaacc atcttgatga atgatcaaga    5520
ggttggtgtg ctagatgcca aggagctagt agacaaggac ggcaccaact tagaactgac    5580
actactcaaa ttgaaccgga atgagaagtt cagagacatc agaggcttct tagccaagga    5640
ggaagtggag gttaatgagg cagtgctagc aattaacacc agcaagtttc ccaacatgta    5700
cattccagta ggacaggtca cagaatacgg cttcttaaac ctaggtggca cacccaccaa    5760
gagaatgctt atgtacaact cccccacaag agcaggccag tgtggtggag tgctcatgtc    5820
caccggcaag gtactgggta tccatgttgg tggaaatggc catcagggct tctcagcagc    5880
actcctcaaa cactacttca atgatgagca aggtgaaata gaatttattg agagctcaaa    5940
ggacgccggg tttccagtca tcaacacacc aagtaaaaca aagttggagc ctagtgtttt    6000
ccaccaggtc tttgagggga caaagaacc agcagtactc aggagtgggg atccacgtct    6060
caaggccaat tttgaagagg ctatattttc caagtatata ggaaatgtca acacacacgt    6120
ggatgagtac atgctggaag cagtggacca ctacgcaggc caactagcca ccctagatat    6180
cagcactgaa ccaatgaaac tggaggacgc agtgtacggt accgagggtc ttgaggcgct    6240
tgatctaaca acgagtgccg gttacccata tgttgcactg ggtatcaaga agagggacat    6300
cctctctaag aagactaagg acctaacaaa gttaaaggaa tgtatggaca agtatgccct    6360
gaacctacca atggtgactt atgtaaaaga tgagctcagg tccatagaga aggtagcgaa    6420
aggaaagtct aggctgattg aggcgtccag tttgaatgat tcagtggcga tgagacagac    6480
atttggtaat ctgtacaaaa ctttccacct aaacccaggg gttgtgactg gtagtgctgt    6540
tgggtgtgac ccagacctct tttgagcaa gataccagtg atgttagatg acatctcat    6600 agcatttgat tactctgggt acgatgctag cttaagccct gtctggtttg cttgcctaaa    6660
aatgttactt gagaagcttg gatacacgca caaagagaca aactacattg actacttgtg    6720
caactcccat cacctgtaca gggataaaca ttactttgtg aggggtggca tgccctcggg    6780
atgttctggt accagtattt tcaactcaat gattaacaat atcataatta ggacactaat    6840
gctaaaagtg tacaaaggga ttgacttgga ccaattcagg atgatcgcat atggtgatga    6900
tgtgatcgca tcgtacccat ggcctataga tgcatcttta ctcgctgaag ctggtaaggg    6960
ttacgggctg atcatgacac cagcagataa gggagagtgc tttaacgaag ttacctggac    7020
caacgtcact ttcctaaaga ggtattttag agcagatgaa cagtacccct tcctggtgca    7080
tcctgttatg cccatgaaag acatacacga atcaattaga tggaccaagg atccaaagaa    7140
```

```
cacccaagat cacgtgcgct cactgtgtct attagcttgg cataacgggg agcacgaata    7200
tgaggagttc atccgtaaaa ttagaagcgt cccagtcgga cgttgtttga ccctccccgc    7260
gttttcaact ctacgcagga agtggttgga ctccttttag attagagaca atttgaaata    7320
atttagattg gcttaaccct actgtgctaa ccgaaccaga taacggtaca gtaggggtaa    7380
attctccgca ttcggtgcg                                                 7399

<210> SEQ ID NO 3
<211> LENGTH: 5031
<212> TYPE: DNA
<213> ORGANISM: Adeno-associated virus

<400> SEQUENCE: 3
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gaattgcctg    240
caggcagctg cgcgctcgct cgctcactga ggccgcccgg gcaaagcccg ggcgtcgggc    300
gacctttggt cgcccggcct cagtgagcga gcgagcgcgc agagagggag tggccaactc    360
catcactagg ggttcctatc gatatcaagc tttaatagta atcaattacg ggtcattag    420 ttcatagccc atatatggag ttccgcgtta cataacttac ggtaaatggc ccgcctggct    480
gaccgcccaa cgacccccgc ccattgacgt caataatgac gtatgttccc atagtaacgc    540
caatagggac tttccattga cgtcaatggg tggagtattt acggtaaact gcccacttgg    600
cagtacatca agtgtatcat atgccaagta cgccccctat tgacgtcaat gacggtaaat    660
ggcccgcctg gcattatgcc cagtacatga ccttatggga cttcctact tggcagtaca    720 tctacgtatt agtcatcgct attaccatgg tgatgcggtt ttggcagtac atcaatgggc    780
gtggatagcg gtttgactca cggggatttc caagtctcca ccccattgac gtcaatggga    840
gtttgttttg gcaccaaaat caacgggact ttccaaaatg tcgtaacaac tccgccccat    900
tgacgcaaat gggcggtagg cgtgtacggt gggaggtcta taagcaga gctggtttag    960 tggatatcct taagggccca gccggcccga atcccggccg ggaacggtgc attggaacgc   1020
ggattccccg tgccaagagt gacgtaagta ccgcctatag agtctatagg cccacaaaaa   1080
atgctttctt cttttaatat acttttttgt ttatcttatt tctaatactt tccctaatct   1140
ctttctttca gggcaataat gatacaatgt atcatgcctc tttgcaccat tctaaagaat   1200
aacagtgata atttctgggt taaggcaata gcaatatttc tgcatataaa tatttctgca   1260
tataaattgt aactgatgta agaggtttca tattgctaat agcagctaca atccagctac   1320
cattctgctt ttatttatg gttgggataa ggctggatta ttctgagtcc aagctaggcc   1380
cttttgctaa tcatgttcat acctcttatc ttcctcccac agctcctggg caacgtgctg   1440
gtctgtgtgc tggcccatca cttggcaaa gaattgggat tcgcgagaat ctctagagt   1500 cgacactagt gcggatccac gggtggcatc cctgtgaccc ctccccagtg cctctcctgg   1560
ccctggaagt tgccactcca gtgcccacca gccttgtcct aataaaatta agttgcatca   1620
ttttgtctga ctaggtgtcc ttctataata ttatggggtg gaggggggtg gtatggagca   1680
aggggcaagt tgggaagaca acctgtaggg cctgcggggt ctattgggaa ccaagctgga   1740
gtgcagtggc acaatcttgg ctcactgcaa tctccgcctc ctgggttcaa gcgattctcc   1800
tgcctcagcc tcccgagttg ttgggattcc aggcatgcat gaccaggctc agctaatttt   1860
```

```
tgttttttg gtagagacgg ggtttcacca tattggccag gctggtctcc aactcctaat    1920
ctcaggtgat ctaccacct tggcctccca aattgctggg attacaggcg tgaaccactg    1980
ctcccttccc tgtccttatc gatagatcta ggaaacccta gtgatggagt tggccactcc   2040
ctctctgcgc gctcgctcgc tcactgaggc cgggcgacca aaggtcgccc gacgcccggg   2100
ctttgcccgg gcggcctcag tgagcgagcg agcgcgcagc tgcctgcagg cagcttggca   2160
ctggccgtcg ttttacaacg tcgtgactgg gaaaaccctg gcgttaccca acttaatcgc   2220
cttgcagcac atccccctt cgccagctgg cgtaatagcg aagaggcccg caccgatcgc    2280
ccttcccaac agttgcgcag cctgaatggc gaatggcgcc tgatgcggta ttttctcctt   2340
acgcatctgt gcggtatttc acaccgcata cgtcaaagca accatagtac gcgccctgta   2400
gcggcgcatt aagcgcggcg ggtgtggtgg ttacgcgcag cgtgaccgct acacttgcca   2460
gcgccctagc gcccgctcct ttcgctttct tcccttcctt tctcgccacg ttcgccggct   2520
ttccccgtca gctctaaat cggggggctcc ctttagggtt ccgatttagt gctttacggc   2580
acctcgaccc caaaaaactt gatttgggtg atggttcacg tagtgggcca tcgccctgat   2640
agacggtttt tcgccctttg acgttggagt ccacgttctt taatagtgga ctcttgttcc   2700
aaactggaac aacactcaac cctatctcgg gctattcttt tgatttataa gggattttgc   2760
cgatttcggc ctattggtta aaaaatgagc tgatttaaca aaaatttaac gcgaatttta   2820
acaaaatatt aacgtttaca attttatggt gcactctcag tacaatctgc tctgatgccg   2880
catagttaag ccagccccga cacccgccaa cacccgctga cgcgccctga cgggcttgtc   2940
tgctcccggc atccgcttac agacaagctg tgaccgtctc cgggagctgc atgtgtcaga   3000
ggttttcacc gtcatcaccg aaacgcgcga cgaaaggg cctcgtgata cgcctatttt    3060
tataggttaa tgtcatgata taatggtt cttagacgtc aggtggcact tttcggggaa    3120
atgtgcgcgg aacccctatt tgtttattt tctaaataca ttcaaatatg tatccgctca    3180
tgagacaata accctgataa atgcttcaat aatattgaaa aaggaagagt atgagtattc   3240
aacatttccg tgtcgccctt attcccttt ttgcggcatt ttgccttcct gttttgtgctc   3300 acccagaaac gctggtgaaa gtaaaagatg ctgaagatca gttgggtgca cgagtgggtt   3360
acatcgaact ggatctcaac agcggtaaga tccttgagag ttttcgcccc gaagaacgtt   3420
ttccaatgat gagcactttt aaagttctgc tatgtggcgc ggtattatcc cgtattgacg   3480
ccgggcaaga gcaactcggt cgccgcatac actattctca gaatgacttg gttgagtact   3540
caccagtcac agaaaagcat cttacggatg gcatgacagt aagagaatta tgcagtgctg   3600
ccataaccat gagtgataac actgcggcca acttacttct gacaacgatc ggaggaccga   3660
aggagctaac cgcttttttg cacaacatgg gggatcatgt aactcgcctt gatcgttggg   3720
aaccggagct gaatgaagcc ataccaaacg acgagcgtga ccacacgatg cctgtagcaa   3780
tggcaacaac gttgcgcaaa ctattaactg gcgaactact tactctagct tcccggcaac   3840
aattaataga ctggatggag gcggataaag ttgcaggacc acttctgcgc tcggcccttc   3900
cggctggctg gtttattgct gataaatctg gagccggtga gcgtgggtct cgcggtatca   3960
ttgcagcact ggggccagat ggtaagccct cccgtatcgt agttatctac acgacgggga   4020
gtcaggcaac tatggatgaa cgaaatagac agatcgctga gataggtgcc tcactgatta   4080
agcattggta actgtcagac caagtttact catatatact ttagattgat ttaaaacttc   4140
atttttaatt taaaaggatc taggtgaaga tccttttga taatctcatg accaaaatcc    4200
cttaacgtga gttttcgttc cactgagcgt cagaccccgt agaaaagatc aaaggatctt   4260
```

-continued

```
cttgagatcc ttttttctg cgcgtaatct gctgcttgca aacaaaaaaa ccaccgctac    4320
cagcggtggt ttgtttgccg gatcaagagc taccaactct ttttccgaag gtaactggct    4380
tcagcagagc gcagatacca aatactgttc ttctagtgta gccgtagtta ggccaccact    4440
tcaagaactc tgtagcaccg cctacatacc tcgctctgct aatcctgtta ccagtggctg    4500
ctgccagtgg cgataagtcg tgtcttaccg ggttggactc aagacgatag ttaccggata    4560
aggcgcagcg gtcgggctga acgggggggtt cgtgcacaca gcccagcttg gagcgaacga    4620
cctacaccga actgagatac ctacagcgtg agctatgaga aagcgccacg cttcccgaag    4680
ggagaaaggc ggacaggtat ccggtaagcg gcagggtcgg aacaggagag cgcacgaggg    4740
agcttccagg gggaaacgcc tggtatcttt atagtcctgt cgggtttcgc cacctctgac    4800
ttgagcgtcg atttttgtga tgctcgtcag gggggcggag cctatggaaa aacgccagca    4860
acgcggcctt tttacggttc ctggccttt gctggccttt tgctcacatg ttctttcctg     4920
cgttatcccc tgattctgtg gataaccgta ttaccgcctt tgagtgagct gataccgctc    4980
gccgcagccg aacgaccgag cgcagcgagt cagtgagcga ggaagcggaa g             5031
```